(12) United States Patent
 Schneider et al.

(10) Patent No.: US 8,560,337 B2
(45) Date of Patent: Oct. 15, 2013

(54) USER INTERFACE FOR GENERATING AND MANAGING MEDICATION TAPERS

(75) Inventors: Charles F. Schneider, Kansas City, MO (US); John Q. Deverter, Liberty, MO (US); Yegor Faridovich Hanov, Fairway, KS (US); Ethan D. Gershon, Raanana (IL)

(73) Assignee: Cerner Innovation, Inc., Kansas City, KS (US)

( * ) Notice: Subject to any disclaimer, the term of this patent is extended or adjusted under 35 U.S.C. 154(b) by 859 days.

(21) Appl. No.: 12/240,608

(22) Filed: Sep. 29, 2008

(65) Prior Publication Data
US 2009/0138814 A1    May 28, 2009

Related U.S. Application Data

(60) Provisional application No. 60/976,224, filed on Sep. 28, 2007.

(51) Int. Cl.
 *G06Q 10/00* (2012.01)
 *G06F 17/30* (2006.01)
(52) U.S. Cl.
 USPC .................................................. 705/2; 707/6
(58) Field of Classification Search
 USPC ............................................................ 705/2
 See application file for complete search history.

(56) References Cited

U.S. PATENT DOCUMENTS

| | | | | |
|---|---|---|---|---|
| 5,758,095 | A | * | 5/1998 | Albaum et al. ............... 705/2 |
| 2004/0172295 | A1 | * | 9/2004 | Dahlin et al. ............... 705/2 |
| 2007/0203907 | A1 | * | 8/2007 | Lee .............................. 707/6 |

OTHER PUBLICATIONS

Final Office Action mailed Feb. 16, 2011 U.S. Appl. No. 12/240,613, filed Sep. 29, 2008 (13 pgs).
Non-final Office Action mailed Sep. 1, 2010 U.S. Appl. No. 12/240,613, filed Sep. 28, 2008 (13 pgs).
Non-final Office Action mailed May 9, 2012 U.S. Appl. No. 12/240,613, 26 pp.
Notice of Allowance in related case U.S. Appl. No. 12/240,613, mailed Aug. 30, 2012, 10 pp.
Akridge, "Get sharp about safety," Healthcare Purchasing News, v33n8, Aug. 2009, pp. 1-356.

\* cited by examiner

*Primary Examiner* — Hiep V Nguyen
(74) *Attorney, Agent, or Firm* — Shook, Hardy & Bacon L.L.P.

(57) ABSTRACT

Methods, computer storage media, systems and user interfaces for generating and/or managing medication tapers are provided. Medication tapers are generated by receiving medication taper data and calculating a planned regimen that includes a set of orders based upon the received medication taper data. Each order of the set of orders may be modified, captured and/or completed, for instance, by a clinician. After a medication taper has been completed, it may be retrieved and managed as desired.

15 Claims, 22 Drawing Sheets

USER INTERFACE FOR GENERATING AND MANAGING MEDICATION TAPERS

CROSS-REFERENCE TO RELATED APPLICATIONS

This application claims the benefit of U.S. Provisional Patent Application No. 60/976,224, filed Sep. 28, 2007, entitled "User Interface for Generating and Managing Medication Tapers."

This application is related by subject matter to U.S. patent application Ser. No. 12/240,613 filed even date herewith and entitled "Generating and Managing Medication Tapers", which is assigned or under obligation of assignment to the same entity as this application, and incorporated in this application by reference.

BACKGROUND

Patients often require a medication prescription that changes over time in dose and/or frequency of administration, i.e., a medication taper. Medication tapers having an increasing or decreasing dose or frequency of administration are beneficial in many circumstances. A decreasing dose or frequency of administration may be beneficial, for example, in instances where a medication must act quickly to combat a specific condition. After the initial higher dose, however, a reduced medication dose or frequency of administration may achieve the desired medical result. Accordingly, a medication taper is desirable to minimize the amount of medication administered to the patient and, yet, maintain effectiveness. In such an instance, the medication taper achieves the desired medical result while it decreases the side effects associated with the medication, the medication expenses, and the amount of medication entering the patient's system.

On the other hand, an increasing dose or frequency of administration may be beneficial, for example, in instances where a medication becomes ineffective at a specific dose or frequency of administration. In such an instance, after the initial administration(s) of a medication, only an increased medication dose or frequency of administration may achieve the desired medical result. Accordingly, a medication taper is desirable to maintain the medication's effectiveness without incurring unnecessary side effects associated with the medication, medication expenses, and amounts of medication entering the patient's system during the initial administration(s) of the medication.

Although medication tapers are oftentimes beneficial, preparing and managing medication tapers is an error-prone and time-consuming practice for clinicians. A clinician preparing a hand-written medication taper is generally required to perform calculations and record various details pertaining to each dosage of the medication taper. Further, although management information systems have played a role in improving the practice of prescribing medications, the clinician may still be required to perform calculations and to input separately each dose of the medication taper in preparing a medication taper. In either case, the opportunity for error is prevalent both in making medication taper calculations and in the potential for inputting or recording duplicative information.

Similarly, managing a medication taper, either by hand-written prescription management or computerized prescription management, also may result in errors and/or inefficiencies. For example, to modify a medication taper, each medication dosage of the medication taper may need to be modified individually. As such, not only is duplicative work by a clinician likely, prescription errors may result if all dosages of the medication taper are not similarly modified.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Utilizing the methods and systems described herein, computerized systems, methods, computer storage media having computer-executable instructions embodied thereon for performing the disclosed methods, and user interfaces for generating a set of orders that defines a medication taper and for managing medication tapers are provided. In one aspect, the present invention provides a user interface embodied on at least one computer-storage medium, the user interface for generating medication tapers. In embodiments, the user interface includes a start dose display area configured to receive one or more data elements pertaining to a first dose of a medication, a taper details display area configured to receive one or more data elements pertaining to a change relative to eth first dose of the medication, a final dose display area configured to receive one or more data elements pertaining to a final dose of the medication, and a selectable calculation indicator display area configured to display a calculation indicator, selection of which initiates calculation of a planned regimen. If desired, the user interface may further include a planned regimen display area configured to display the planned regimen, the planned regimen including a set of orders defining a medication taper for the medication, and/or an order details display area configured to display one or more order details and detail values pertaining to the planned regimen.

In another aspect, the present invention provides a user interface embodied on at least one computer storage medium, the user interface for managing medication tapers. In embodiments, the user interface includes an orders display area displaying one or more orders associated with a patient's electronic medical record, at least one of the orders having an indicator associated therewith indicating the at least one order comprises a set of orders defining a medication taper, and a status indicator display area displaying a status of each order displayed in the orders display area. The at least one order includes a selectable indicator associated therewith that, upon selection, initiates display of one or more additional details associated with the medication taper.

BRIEF DESCRIPTION OF THE SEVERAL VIEWS OF THE DRAWINGS

The present invention is described in detail below with reference to the attached drawing figures, wherein:

FIG. 5 is an illustrative screen display, in accordance with an embodiment of the present invention, showing a prescription ordering service;

FIG. 6 is an illustrative screen display of an exemplary user interface for viewing a medication order, in accordance with an embodiment of the present invention;

FIG. 11 is an illustrative screen display of an exemplary user interface for viewing a planned regimen (i.e., medication taper), in accordance with an embodiment of the present invention;

FIG. 13 is an illustrative screen display of an exemplary user interface for viewing a medication taper worksheet upon saving the medication taper to a favorites folder, in accordance with an embodiment of the present invention;

FIG. 15 is an illustrative screen display, in accordance with an embodiment of the present invention, of an exemplary user interface showing a prescription ordering service;

FIG. 16 is an illustrative screen display of an exemplary user interface for viewing a medication taper, in accordance with an embodiment of the present invention;

FIG. 17 is an illustrative screen display of an exemplary user interface for viewing an expanded view of a medication taper, in accordance with an embodiment of the present invention;

FIG. 18 is an illustrative screen display of an exemplary user interface for viewing options for modifying the medication taper, in accordance with an embodiment of the present invention; and FIG. 19 is an illustrative screen display of an exemplary user interface for viewing options that may be utilized to modify a medication order, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for generating and managing medication tapers. Utilizing the methods and systems described herein, a set of orders defining a medication taper is generated by receiving medication taper data (e.g., a medication identifier, one or more medication doses, one or more frequencies of administration, and the like), for instance, utilizing a medication taper worksheet, and calculating a planned regimen based upon the received data, the planned regimen including the set of orders. If desired, one or more of the orders comprising the medication taper may be modified, captured and/or completed, e.g., by a clinician. After the medication taper has been completed, a clinician may retrieve and/or manage (e.g., modify) the medication taper as desired.

Having briefly described embodiments of the present invention, an exemplary operating environment suitable for use in implementing embodiments of the present invention is described below.

Figure 1:
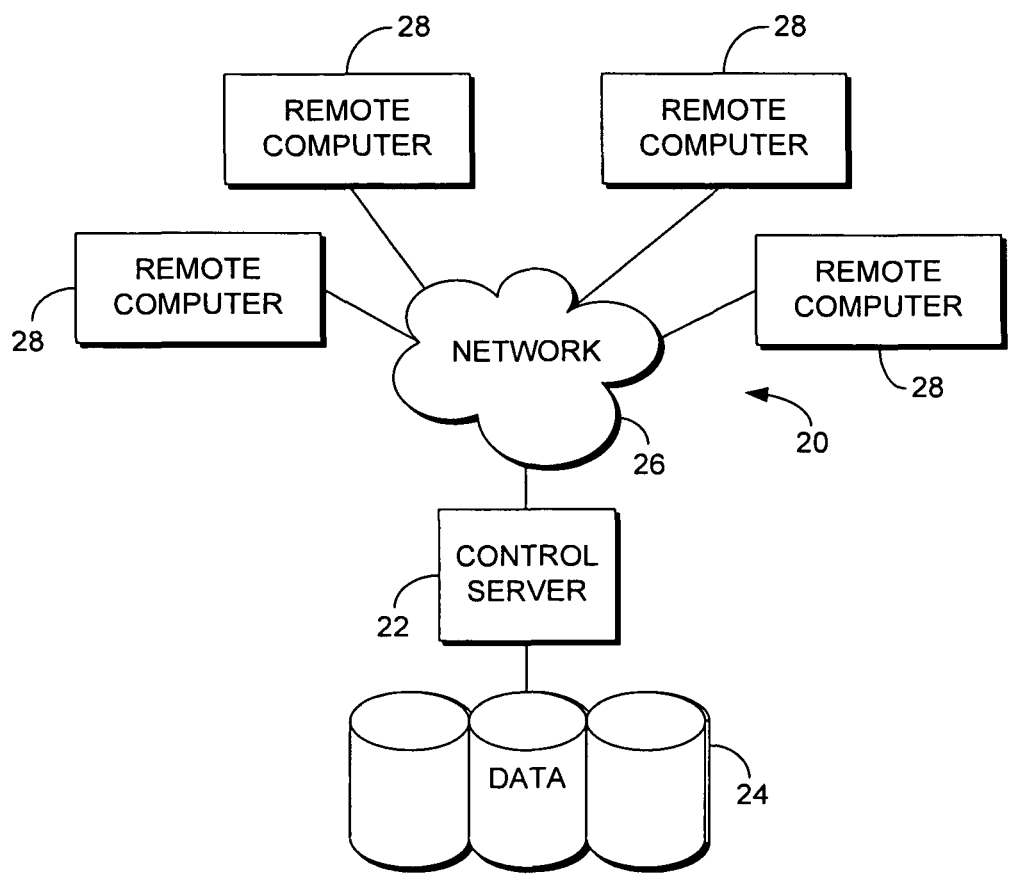
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare-related orders, particularly, sets of orders that define medication tapers. As contemplated by the language above, the methods and systems of embodiments of the present invention may also be implemented on a stand-alone desktop, personal computer, or any other computing device used in a healthcare environment or any of a number of other locations.

As previously mentioned, embodiments of the present invention relate to methods, systems, and computer-readable media for use in, e.g., a healthcare environment, for generating and/or managing sets of orders that define medication tapers. For simplicity, the particular user will often be referred to herein as a clinician. However, it will be understood that the particular user may be any healthcare professional, physician, or other provider, as described above.

As used herein, the term "medication order" refers to a medication prescription having a dose and frequency that does not change over time. The term "medication taper," as used herein, refers to two or more medication orders having relative increasing or decreasing medication doses and/or frequencies of administration. For example, a medication taper may include a medication order having a medication dose of 400 mcg and a medication order having a medication dose of 300 mcg.

Figure 2:
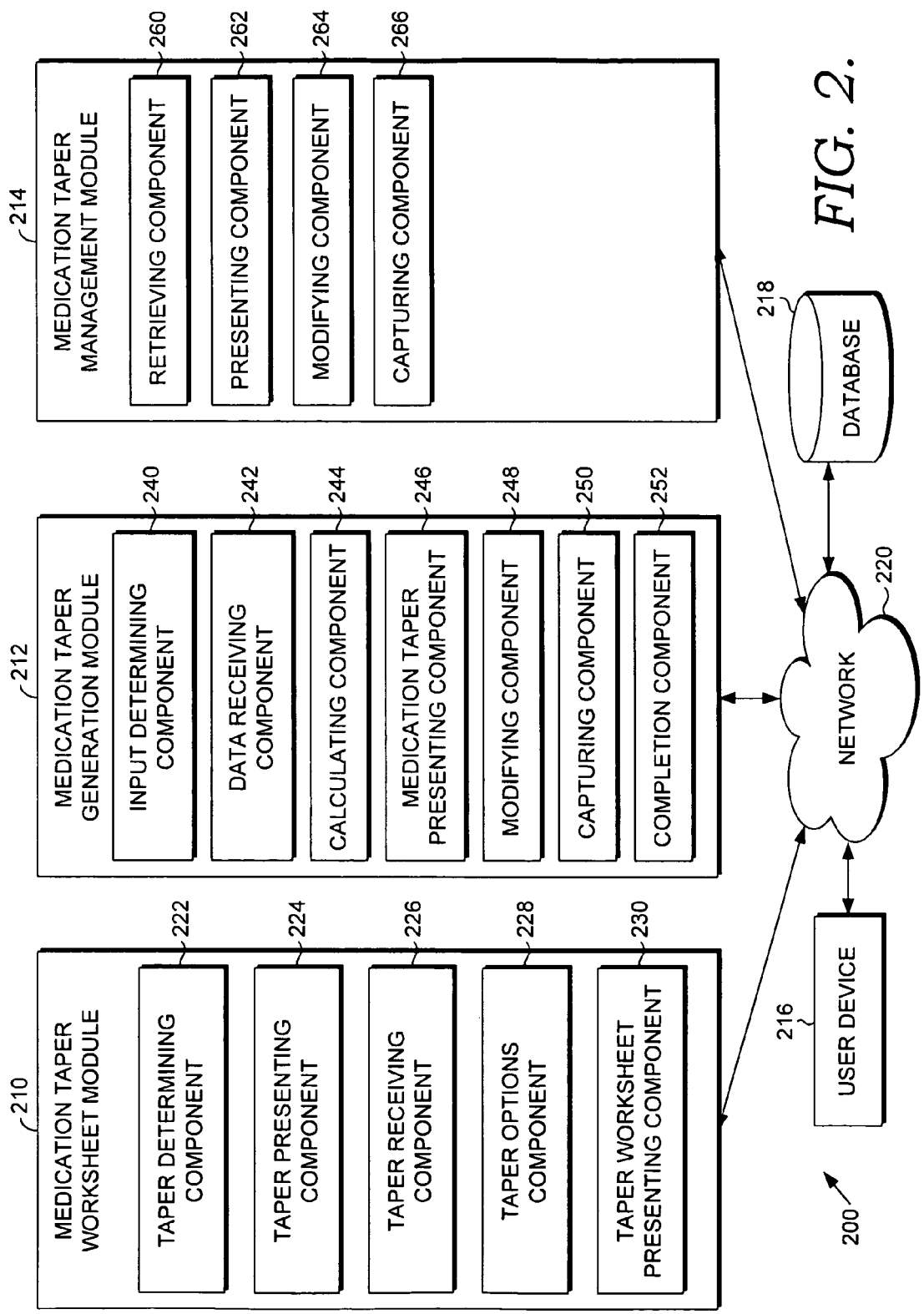
FIG. 2 is a block diagram of an exemplary computing system suitable for use in implementing embodiments of the present invention.

With reference to FIG. 2, an exemplary system suitable for use in implementing embodiments of the present invention is shown and designated generally as reference numeral 200. System 200 includes a medication taper worksheet module 210, a medication taper generation module 212, a medication taper management module 214, a user device 216, and a database 218, all in communication with one another through a network 220. The network 220 may include, without limitation, one or more local area networks (LANs) and/or wide area networks (WANs). Such networking environments are commonplace in offices, enterprise-wide computer networks, intranets, and the Internet. Accordingly, the network 220 is not further described herein.

The database 218 is configured to store information associated with at least one medication. In various embodiments, such information may include, without limitation, a medication name, dose, dose unit, routes of administration, frequency of administration, dose start date/time, final dose date/time, and the like. In embodiments, the database 218 is configured to be searchable for one or more medications, medication orders, medication tapers, patients, and/or associated values stored in association therewith. It will be understood and appreciated by those of ordinary skill in the art that the information stored in the database 218 may be configurable and may include any information relevant to a medications, medication orders, medication tapers, and/or a case or patient associated therewith. The content and volume of such information are not intended to limit the scope of embodiments of the present invention in any way. Further, though illustrated as a single, independent component, database 218 may, in fact, be a plurality of databases, for instance, a database cluster, portions of which may reside on a computing device associated with the medication taper worksheet module 210, the medication taper generation module 212, the medication taper management module 214, the user device 216, another external computing device (not shown) and/or any combination thereof.

The medication taper worksheet module 210 includes various components and is configured to generate a medication taper worksheet. The medication taper worksheet module 210 includes a taper determining component 222, a taper presenting component 224, a taper receiving component 226, a taper options component 228, and a taper worksheet presenting component 230.

The taper determining component 222 is configured to determine the appropriateness of a medication taper. In one embodiment, medication tapers may be deemed appropriate for all medications. In an alternative embodiment, the appropriateness of a medication taper may depend upon the desired medication. In such an embodiment, in one instance, prior to taper determining component 222 determining the appropriateness of a medication taper, a clinician may have specified a medication. The specified medication, in one instance, may be associated with a patient. (The terms "individual," "person," and "patient" are used interchangeably herein and are not meant to limit the nature of the referenced individual in any way. Rather, the methods and systems described herein are equally applicable, for instance, in a veterinary setting. Further, use herein of the term "patient" is not meant to imply any particular relationship between the individual in question and those generating medication tapers, modifying medication tapers, and the like). The clinician may specify a medication, patient, or combination thereof, for example, by performing a search for the medication or patient or by selecting the medication or patient listed within a menu.

The taper presenting component 224 is configured to present a taper availability notice in instances where a medication taper is deemed appropriate. A taper availability notice indicates that a medication taper may be generated, if the clinician so desires. A taper availability notice presented to a clinician may include, for example, an icon, a sound, text, a value, a selectable "generate taper" button, or a unique formatting thereof. Further, the taper availability notice may be selectable such that a clinician may select the taper availability notice to initiate the generation of a medication taper. In an embodiment where medication tapers are deemed appropriate for all medications, a taper availability notice may be presented in each instance that medical information system 20 of FIG. 1 is accessed or upon selection of a specific medication. For example, an icon representing a medication taper may be presented in association with each instance where a clinician accesses the medical information system 20 of FIG. 1 to prepare a medication order. In such an embodiment, a component, such as taper determining component 222, may then determine whether a medication taper is clinically appropriate and, if a medication taper is not clinically appropriate, present an error message notifying the clinician that a medication taper is unavailable.

The taper receiving component 226 is configured to receive an indication to generate a medication taper. In one embodiment, taper receiving component 226 may receive an indication to generate a medication taper upon a clinician indicating such a desire. For example, a clinician may select a taper availability notice, such as an icon, to indicate a desire to generate a medication taper. Alternatively, taper receiving component 226 may automatically receive an indication to generate a medication taper in association with each instance that medical information computer system 20 of FIG. 1 is accessed, a medication or patient is selected, or a medication order is initiated.

The taper options component 228 is configured to determine medication taper options to present within the medication taper worksheet. In one embodiment, taper options component 228 may determine medication taper options based upon the medication for which a taper is desired, e.g., only medically appropriate options for a specific medication may be presented within the medication taper worksheet. For example, a specific medication may only be available to administer orally. In such a case, taper options component 228 may determine that an oral administration option, e.g., "PO," may be the only medication "route" option to present within the medication taper worksheet. In another embodiment, taper option component 228 may determine that either all medication taper options may be included in the medication taper worksheet as options to the clinician or that no medication taper options should be included in the medication taper worksheet. In such an embodiment, a component, such as data receiving component 242 of medication taper generation module 212, discussed hereinafter, may determine, based upon the clinician's input or selection of an option, whether a medication taper option is clinically appropriate and, if a medication taper option is not clinically appropriate, present an error message notifying the clinician of the error.

The taper worksheet presenting component 230 is configured to present a medication taper worksheet including any medication taper options identified by taper options component 228. The medication taper worksheet may include one or more medication taper fields having default data. As used herein, the term "data" is used to refer to one or more pieces of information. In one embodiment, default data may be based on a specification by a clinician, system developer, system administrator, or the like. In such an embodiment, the clinician, system developer, or system administrator may specify the desired default data for particular medication taper fields. By way of example only, a system developer may default the taper increment or decrement field to "reduce," the unit of measure for the decreasing dose and the final dose to the unit of measure selected by the clinician as the start dose unit of measure, and the start dose date/time to the date/time the taper worksheet is presented.

Alternatively, default data included in a medication taper worksheet may be based on an associated medication order. For example, a specific medication order may be selected at the time an indication to generate a medication taper is received. In such a case, data from the selected medication order may be automatically input into corresponding medication taper fields. Some embodiments may restrict the medication taper fields that may include default data, e.g., only fields pertaining to the start of the dosage may include default data, or may restrict the default data that may be included in a medication taper field. For example, in an instance where default data is based on an associated medication order having a "stat" priority, only the first medication order of the medication taper may default to "stat" priority and all other medication orders of the medication taper may not have default data or may default to another priority, such as "routine" priority. Although some medication taper worksheets may include default data, some embodiments may permit the clinician to modify the default data. In such an embodiment, the clinician modifications may be limited to clinically appropriate modifications.

Figure 3:
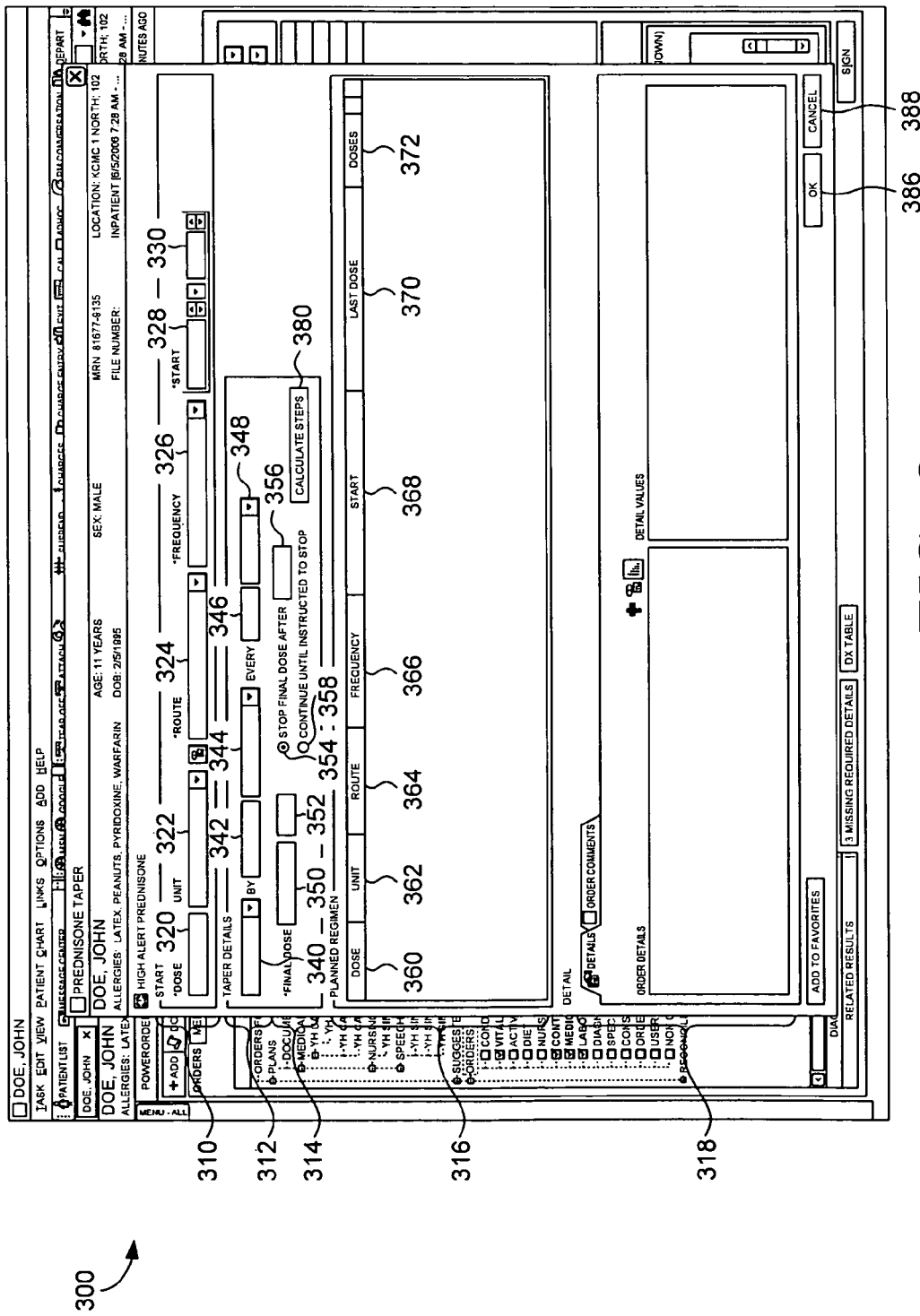
FIG. 3 is an illustrative screen display of an exemplary medication taper worksheet user interface, in accordance with an embodiment of the present invention.

With reference to FIG. 3, an illustrative screen display of an exemplary medication taper worksheet user interface, in accordance with an embodiment of the present invention, is illustrated and designated generally as reference numeral 300. The medication taper worksheet may be associated with a patient, a clinician, a medication, a medication order, or a combination thereof. Screen display 300 includes a start dose area 310, a taper details area 312, a final dose area 314, a planned regimen area 316, and an order details area 318. One skilled in the art will recognize that any and all such combinations of areas, as well as additional similar areas, are contemplated to be within the scope here.

Start dose area 310 is configured to permit a clinician to input data pertaining to the beginning of a medication taper. In the illustrated embodiment, start dose area 310 includes a dose field 320, a unit field 322, a route field 324, a frequency field 326, a start date field 328, and a start time field 330. The dose field 320 is configured to permit a clinician to indicate the desired starting dose, e.g., 300. The unit field 322 is configured to permit a clinician to indicate the desired unit of the starting dose, e.g., mcg. The route field 324 is configured to permit a clinician to indicate the desired medication administration route, e.g., PO. The frequency field 326 is configured to permit a clinician to indicate the desired frequency of the medication administration, e.g., one time a day. The start date field 328 is configured to permit a clinician to indicate the desired day to begin the medication administration, e.g., Jan. 25, 2007. The start time field 330 is configured to permit a clinician to indicate the desired time to begin the medication administration, e.g., 1708 (military time).

Taper details area 312 is configured to permit a clinician to input data pertaining to the increment or decrement of the medication taper. In the illustrated embodiment, taper details area 312 includes a reduce/increase field 340, a taper dose field 342, a taper dose unit field 344, a dose duration field 346, and a dose duration unit field 348. The reduce/increase field 340 is configured to permit a clinician to indicate whether the medication taper is to increase or decrease, e.g., reduce. The taper dose field 342 is configured to permit a clinician to indicate the dose amount of which to increase or decrease the starting dose, e.g., 50. Taper dose unit field 344 is configured to permit a clinician to indicate the unit of the increasing or decreasing dose, e.g., mcg. The dose duration field 346 is configured to permit a clinician to indicate the duration after which the increase or decrease is to occur, e.g., 2. The dose duration unit field 348 is configured to permit a clinician to indicate the unit of the duration after which the increase or decrease is to occur, e.g., days.

Final dose area 314 is configured to permit a clinician to input data pertaining to the final dose. In the illustrated embodiment, final dose area 314 includes a final dose field 350, a final dose unit field 352, a stop field 354, a stop duration field 356, and a continuation field 358. The final dose field 350 is configured to permit a clinician to indicate the final dosage amount, e.g., 100. The final dose unit field 352 is configured to permit a clinician to indicate the unit of the final dosage amount, e.g., mcg. The stop field 354 is configured to permit a clinician to indicate that the final dose should be stopped after a specified time. The stop duration field 356 is configured to permit a clinician to indicate the duration after which the final dose is to stop, e.g., 7. The duration unit will, by default, be equivalent to the unit selected in dose duration unit field 348. The continuation field 360 is configured to permit a clinician to indicate that the final dose should continue until instructed to stop at a later time.

The planned regimen area 316 is configured to display a planned regimen that is calculated based on the start dose data, the taper details data, and the final dose data. Planned regimen area 316 may include, for example, a dose listing 360 (under the heading "dose"), a unit listing 362 (under the heading "unit"), a route listing 364 (under the heading "route"), a frequency listing 366 (under the heading "frequency"), a start listing 368 (under the heading "start"), a last dose listing 370 (under the heading "last dose"), and a number of doses listing 372 (under the heading "doses"). The dose listing 360 is configured to list the dose amounts of the medication orders that comprise the medication taper. The unit listing 362 is configured to list the units that correspond with each dose amount. The route listing 364 is configured to list the administration routes associated with each dose amount. The frequency listing 366 is configured to list the frequencies of administration associated with each dose amount. The start listing 368 is configured to list each start date, time, and location associated with each dose amount. The last dose listing 370 is configured to list each last dose date, time, and location associated with each dose amount. The number of doses listing 372 is configured to list the number of doses associated with each dose amount.

The order details area 318 is configured to display details and detail values pertaining to the medication taper. In one embodiment, order details area 318 may include, for example, freetext orderable, dose, drug form, route of administration, frequency, frequency schedule ID, adhoc frequency instance, prn, pharmacy order priority, first dose date and time, next dose date and time, duration, associated detail values, and the like.

In addition to the start dose area 310, the taper details area 312, the final dose area 314, the planned regimen area 316, and the order details area 318 configured to either permit a clinician to input data or display data, screen display 300 also includes functionality icons. As illustrated, screen display 300 includes a calculation button 380, a medication taper submission button 386, and a medication taper cancellation button 388. The calculation button 380 is configured to permit a clinician to indicate a desire to calculate a planned regimen. The medication taper submission button 386 is configured to permit a clinician to indicate a desire to submit the medication taper. The medication taper cancellation button 388 is configured to permit a clinician to indicate a desire to cancel the medication taper. If desired, the screen display 300 may additionally include a medication order adding button (not shown) configured to permit a clinician to indicate a desire to add a medication order to the medication taper and/or a medication order deleting button (not shown) configured to permit a clinician to indicate a desire to delete a medication order from the medication taper.

Referring back to FIG. 2, the medication taper generation module 212 includes various components and is configured to generate one or more medication tapers. In some embodiments, the medication taper worksheet generated and presented by the medication taper worksheet module 210 may be utilized by the medication taper generation module 212 to generate one or more medication tapers. In other embodiments, any medication taper worksheet that allows a clinician to input data may be utilized by the medication taper generation module 212 to generate one or more medication tapers. The medication taper generation module 212 includes an input determining component 240, a data receiving component 242, a calculating component 244, a medication taper presenting component 246, a modifying component 248, a capturing component 250, and a completion component 252.

The input determining component 240 is configured to determine one or more medication taper fields for which data must be received for calculating component 244 to calculate the planned regimen. In one embodiment, input determining component 240 may determine that all medication taper fields must receive input, such as clinician input data or default input data. The input determining component 240 may also be configured to determine whether data has been input into all required medication taper fields and, if so, enable a calculation function upon receiving input data for each required medication taper field. For example, upon proper completion of each required medication taper field, a "calculate steps" button may be enabled such that a clinician may select the "calculate steps" button to initiate the planned regimen calculation. In some embodiments, input determining component 240 may also be configured to ensure that the input data is clinically appropriate.

The data receiving component 242 may be configured to receive an indication to initiate the calculation function and receive data associated with the medication taper so that a calculation may be performed by calculating component 244. Data receiving component 242 may receive an indication to initiate the calculation function and may receive data associated with the medication taper upon a clinician's selection to calculate the planned regimen. For example, a clinician may select an enabled "calculate steps" button and, thereafter, all data input into medication taper fields may be received by data receiving component 242. Data receiving component 242 may receive one or more data associated with medication taper data, e.g., start dose data, taper details data, and final dose data. In one embodiment, data receiving component 242 may receive data for each medication taper field determined to be required by input determining component 240. In some embodiments, data receiving component 242 may also be configured to determine that all required medication taper fields received input, ensure that the input data is clinically appropriate, or a combination thereof.

The calculating component 244 is configured to calculate a planned regimen based on the medication taper data received by data receiving component 242. In one embodiment, calculating component 244 may calculate each dosage for each medication order, the start date/time for each medication order, the end date/time for each medication order, and the total number of doses of each medication order. In such an embodiment, calculating component 244 may perform all calculations for the first medication order followed by all calculations for the next medication order. Calculating component 244 may proceed by calculating each subsequent medication order until the final medication order of the planned regimen is calculated.

The medication taper presenting component 246 is configured to present the planned regimen and/or the order details that are associated with the medication taper. In one embodiment, the planned regimen and order details pertaining to each medication order may be presented upon the calculation of each medication order. In another embodiment, the planned regimen and order details pertaining to each medication order may only be presented upon calculation of the entire planned regimen.

The modifying component 248 may be configured to receive an indication to initiate a modification and to modify the medication taper. Modifying component 248 may also be configured to present the modified planned regimen, order details, or a combination thereof. The modifying component 248 may receive an indication to initiate a modification based on a clinician's indication to modify, e.g., a clinician's selection of a medication order, a medication order adding button, a medication order deleting button, or the like. Upon receiving an indication to initiate a modification, the modifying component 248 may modify the medication taper by, for example, adding a medication order to the medication taper, deleting a medication order from the medication taper, or changing a medication order. In some embodiments, the modifying component 248 may be configured to receive a modification, e.g., modifications input by a clinician. In instances where the medication order row is selected, a clinician may, for example, change medication taper data that is specific to the selected order, delete the selected order, or add a medication order above or below the selected order. In addition, the modifying component 248 may also be configured to update the order details based on the modifications.

In embodiments permitting a medication order to be added to or removed from the medication taper, the modifying component 248 may default to the last medication order. In such an embodiment, where a clinician selects to add a medication order to the taper order, a new medication order row is added to the bottom of the planned taper regimen. The new medication order row may include default data, such as data based on the start dose data and taper details data, or a combination thereof. For example, upon receiving an indication to add a medication order to the medication taper, a new medication order row may include, based on the previous medication order, the unit measure set forth in the previous unit field; the route set forth in the previous route field; the frequency set forth in the previous frequency field; the start date/time based on the previous medication order as well as the taper duration and associated unit fields; the last dose based on the start date/time of the new medication order; and the number of doses based on the new medication order. In such a case, the dose field may not have a default so that a clinician may input a dose or select a dose in, for example, the order details area. On the other hand, where a clinician selects to remove a medication order, the last medication order of the medication taper is the medication order removed.

The capturing component 250 is configured to capture the medication taper such that the medication taper may be accessed at a later time. The medication taper may be captured automatically or upon receiving an indication to capture the medication taper, e.g., a clinician selects "Add to Favorites" button. The capturing component 250 may present a capturing dialogue to allow a clinician to specify the name of the medication taper, the folder location for saving the medication taper, or a combination thereof. In the embodiment where a capturing dialogue is presented, a default medication taper name and/or default folder location may be specified. For example, the default name may be the drug name followed by the word "Taper" with the starting dose and final dose in parenthesis, e.g., "Drug Taper (50 mg-2.5 mg)." In such an embodiment, although a default medication taper name and/or default folder location may be specified, the clinician may be permitted to modify the medication taper name or the default folder location.

The completion component 252 is configured to complete the medication taper. The completion component 252 may be initiated upon receiving an indication to complete the medication taper, e.g., clinician may select to complete the medication taper. For example, in one embodiment, the clinician may select the "OK" button to indicate a desire to complete the medication taper. To complete the medication taper, the completion component 252 may present the medication taper to an orders queue, the patient's order profile, or other location within the medical information computing system. In the orders queue and the patient's order profile, the medication tapers may be grouped by the medication taper header row, e.g., the drug name followed "Taper." In such an embodiment, the medication taper regimen may be collapsed such that only the medication taper header row is displayed. To view the contents of the entire medication taper, for example, the clinician may select an icon, e.g., a plus sign, located adjacent to the medication taper header row. In addition to presenting the medication taper to the orders queue, the patient's order profile, or other location within the medical information computing system, the completion component 252 may also close the medication taper worksheet.

The taper management module 214 includes various components and is configured to manage one or more medication tapers. The taper management module 214 includes a retrieving component 260, a presenting component 262, a modifying component 264, and a capturing component 266. The retrieving component 260 is configured to retrieve a medication taper. A medication taper may be retrieved from a patient's order profile, an order queue, a favorites folder, or the like. The specific medication taper to be retrieved by the retrieving component 260 may be determined based on a clinician's selection within a menu or a search function.

The presenting component 262 is configured to present the retrieved medication taper. In one embodiment, the presented medication taper regimen may be collapsed such that only the medication taper header row is displayed. To view the contents of the entire medication taper, the clinician may select, for example, an icon, e.g., a plus sign, located adjacent to the medication taper header row.

The modifying component 264 is configured to receive an indication of a desired modification and modify the medication taper. The modifying component 264 may receive an indication of a desired modification based on a clinician's selection of a modification. In some embodiments, prior to receiving an indication of a desired modification, modifying component 264 may be configured to receive an indication to present modification options and present the modification options. For example, in such an embodiment, an indication to present modification options may be received upon a clinician right clicking on a medication order. The modification options may then be presented to the clinician and, subsequently, the clinician may select the desired modification option. The modifying component 264 then receives an indication of the desired modification and, thereafter, modifies the medication taper.

Medication tapers may be modified by modifying medication orders as a group, individually, or a combination thereof. The modifying component 264 may modify the medication taper by, for example, canceling, discontinuing, voiding, modifying, suspending, copying, rescheduling, changing administration times, and the like. Discontinuing or canceling a medication taper may occur in instances, for example, where a patient is not responding to the medication and, accordingly, stopping the valid regimen is desirable. In instances where the desired modification is canceling or discontinuing, in one embodiment, the modifying component 264 may determine if the canceling preference is set to optional, required, or off. In such an embodiment, if the canceling preference is set to off, the modifying component 264 may cancel all the medication orders within the medication taper. If, however, the canceling preference is set to optional or required, the modifying component 264 may be configured to present a dialogue box that prompts for the cancel or discontinue reason. The modifying component 264 may also be configured to receive clinician input of the cancel or discontinue reason.

Further, in some embodiments, the modifying component 264 may also be configured to present an option to the clinician to select one or more medication orders to retain and to receive input indicating one or more medication orders to retain. One skilled in the art will appreciate that the modifying component 264 may, among other things, present dialogue boxes, receive indications and data, cancel one or more medication orders or medication tapers, retain one or more medication orders or medication tapers, and update one or more medication orders or medication tapers with a cancel or discontinue reason.

Voiding a medication taper may occur in instances where the medication taper is associated with the wrong patient and, thus, it is an invalid medication taper. In instances where the desired modification is voiding, in one embodiment, the modifying component 264 may check void privileges and determine whether to void the medication taper. If it is determined that the medication taper should not be voided, the void action may be disabled by the modifying component 264. If it is determined that the medication taper may be voided, the medication taper may be voided by the modifying component 264.

One skilled in the art will recognize that the modifying component 264 may be configured to perform numerous modifications in a plurality of methods. For example, in instances where the desired modification is resetting the taper regimen, modifying component 264 may be configured to evaluate details with pending modifications and revert changes. In instances where the desired modification is modifying the medication taper, the modifying component 264 may be configured to present the medication taper in modifiable form, and receive modifications. The examples of modifications and methods of modifications presented herein are not intended to limit the scope of this patent application.

The capturing component 266 is configured to capture modifications to the medication taper order. Capturing component may also be configured to present the medication taper to the orders queue, the patient's order profile, or other location within the medical information computing system.

As previously mentioned, the system 200 further includes a user device 216 in communication with the database 218, the medication taper worksheet module 210, the medication taper generation module 212, and the medication taper management module 214 via the network 220. The user device 216 may be associated with any type of computing device, such as computing device 100 described with reference to FIG. 1, for example. Though not shown in FIG. 2, the user device 216 typically includes at least one presentation module configured to present (e.g. display) one or more worksheets and/or results associated with a medication taper. In this regard, the presentation module may be configured to receive taper worksheets, for instance, from database 218, and utilize such taper worksheets to receive input of medication taper data.

It will be understood and appreciated by those of ordinary skill in the art that other components not shown may also be included with the system 200. Further, additional components not shown may also be included within any of the database 218, the taper worksheet module 210, the taper generation module 212, the taper management module 214, and the user device 216. Additionally, any components illustrated in FIG. 2 in association with the taper worksheet module 210, the taper generation module 212, the taper management module 214 may additionally or alternatively be associated with any of the other illustrated modules, the user device 216, and/or another external computing device, e.g., a server (not shown). Any and all such variations are contemplated to be within the scope of embodiments hereof.

Figure 4:
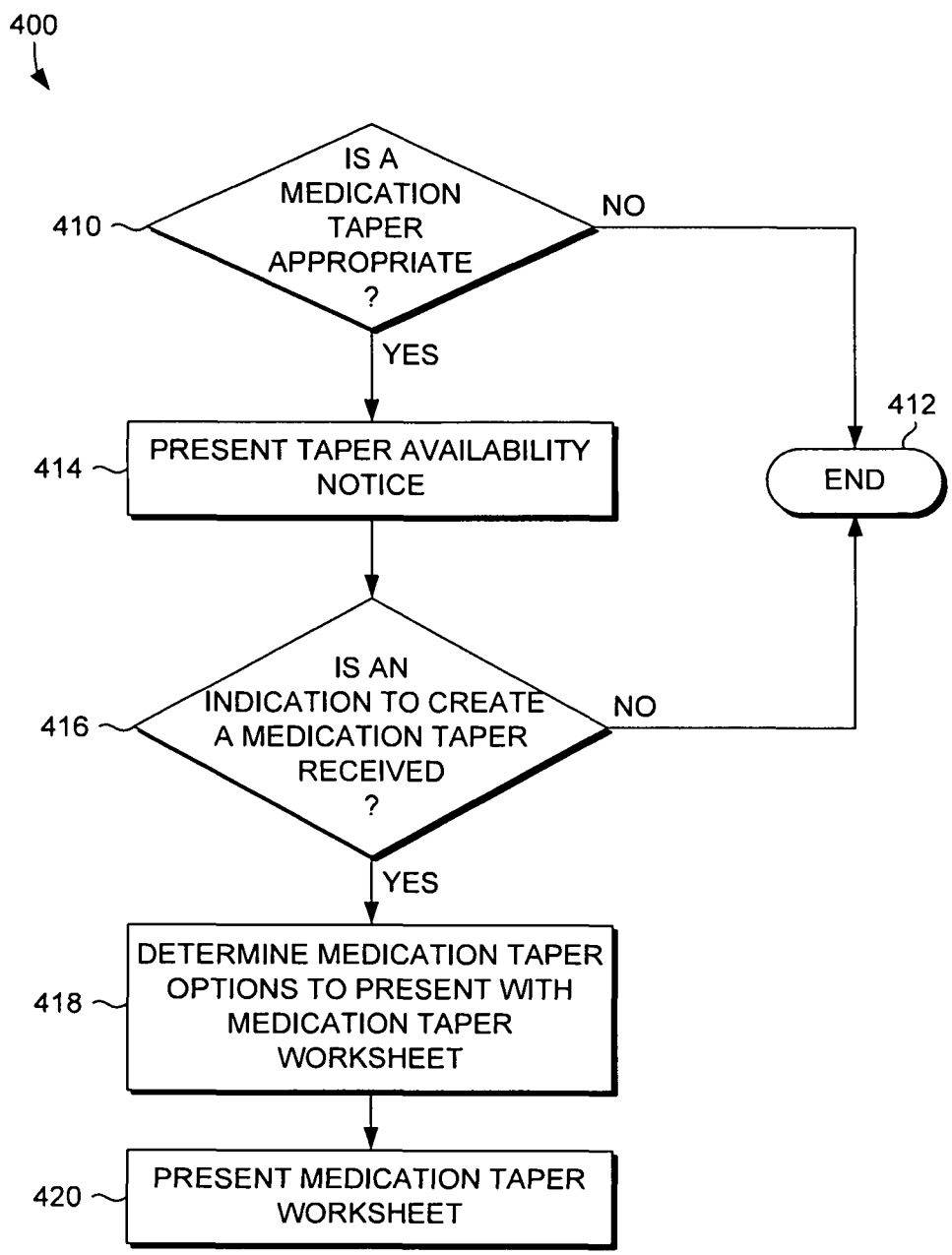
FIGS. 4 is a flow diagram showing a method for generating a medication taper worksheet, in accordance with an embodiment of the present invention.

Turning now to FIG. 4, a flow diagram showing a method for generating a taper worksheet, in accordance with an embodiment of the present invention, is illustrated and designated generally as reference numeral 400. Method 400 may be implemented on the above-described exemplary computing system environment (FIG. 1) and, by way of example only, may be utilized by a clinician to prepare and/or order a medication taper.

Initially, as indicated at block 410, the appropriateness of a medication taper is determined. If it is determined that a medication taper is not appropriate, the method ends, as indicated at block 412. If, however, it is determined that a medication taper is appropriate, a taper availability notice is subsequently presented at block 414 to indicate that a medication taper may be generated if desired. At block 416, it is determined whether an indication to generate a medication taper is received. If it is determined that an indication to generate a medication taper is not received, the method ends, as indicated at block 412. If, however, it is determined that an indication to generate a medication taper is received, e.g., a clinician selects a taper availability notice, the medication taper options to present within the medication taper worksheet are determined. This is indicated at block 418. Subsequently, as indicated at block 420, the medication taper worksheet, including any medication taper options identified at block 418, is presented.

Figure 5:
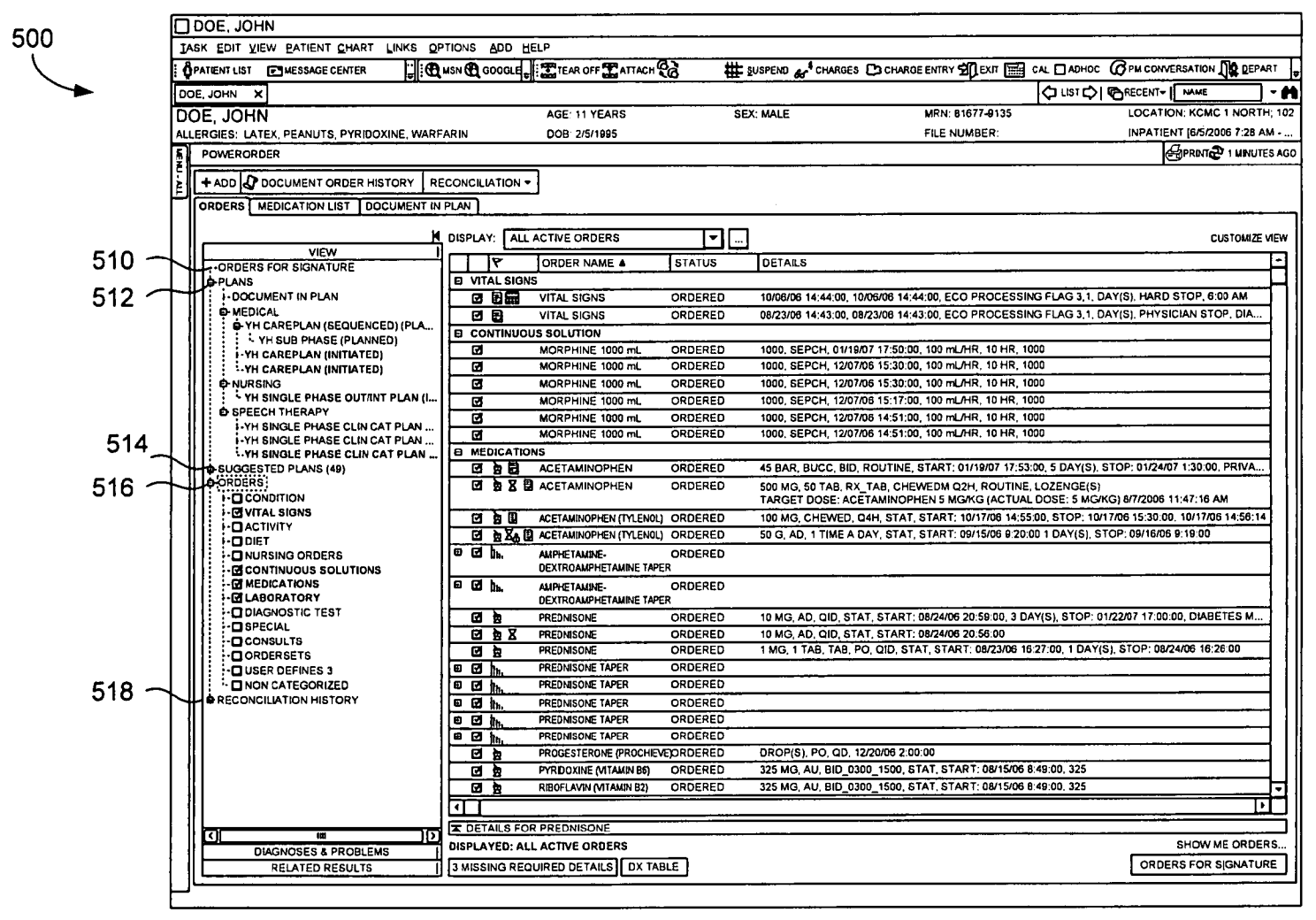
Figure 6:
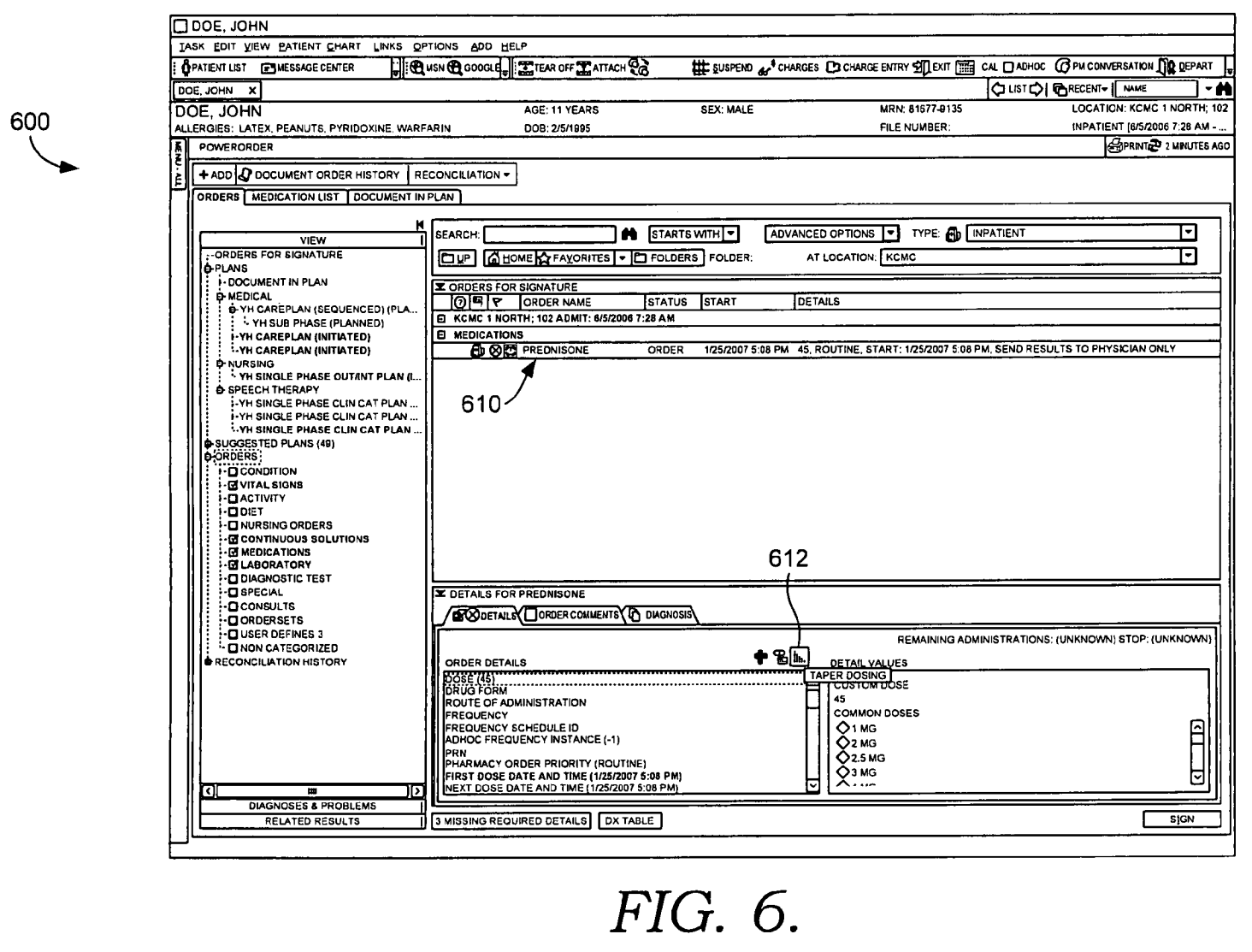
Figure 7:
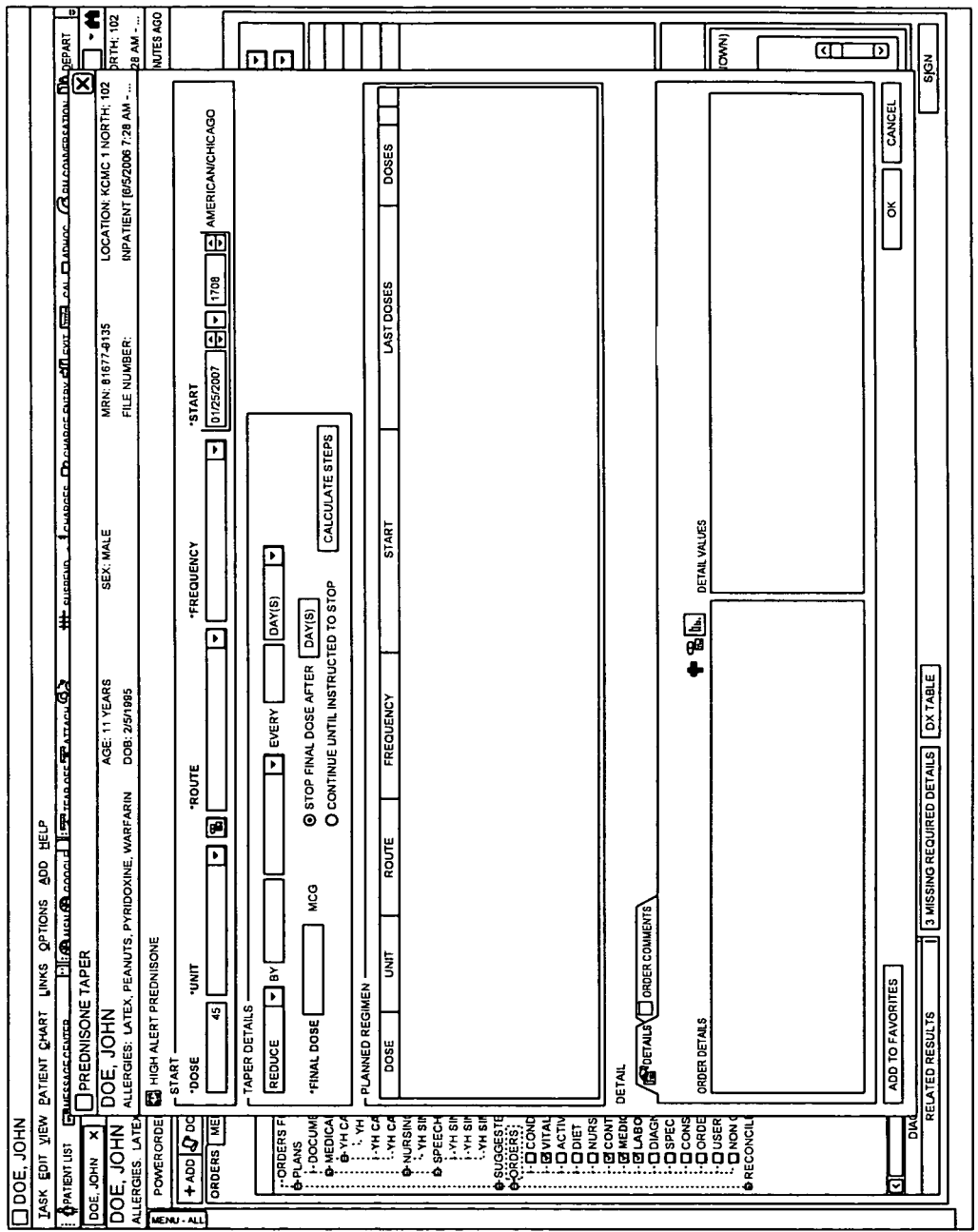
FIG. 7 is an illustrative screen display, in accordance with an embodiment of the present invention, of an exemplary user interface for viewing a medication taper worksheet.
Figure 8A:
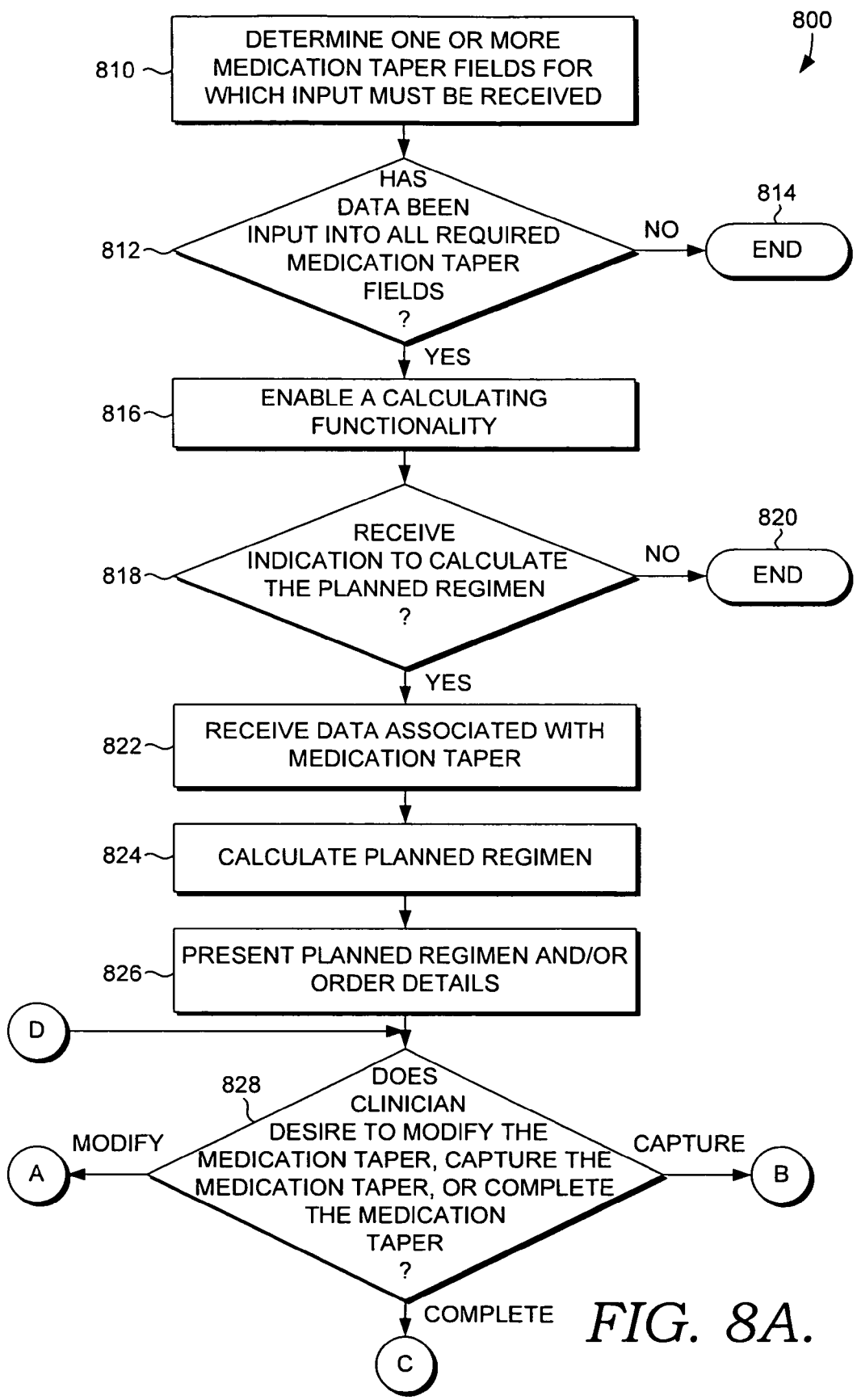
FIGS. 8A-8D are a flow diagram showing a method for generating a medication taper, in accordance with an embodiment of the present invention.
Figure 8B:
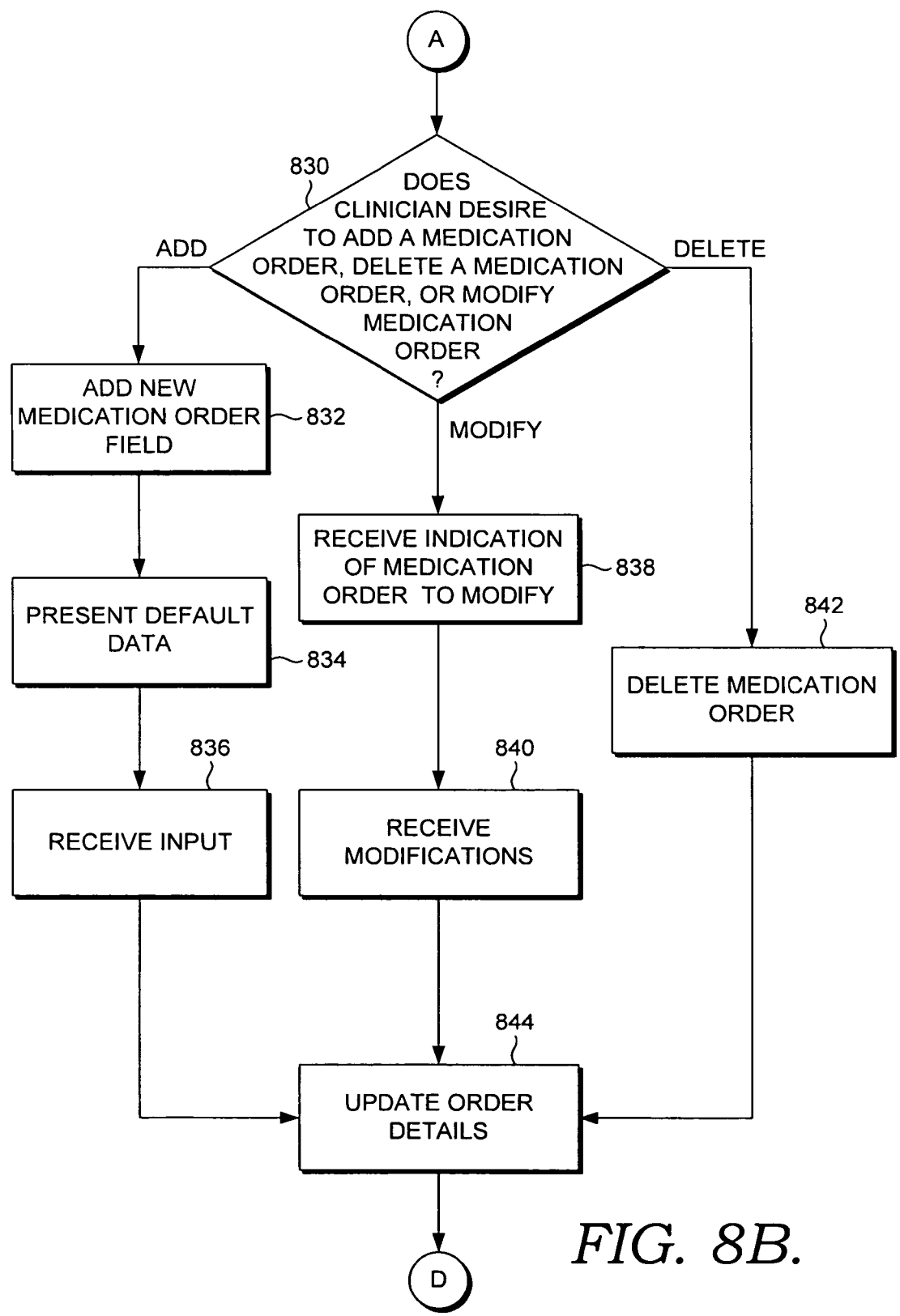
Figure 8C:
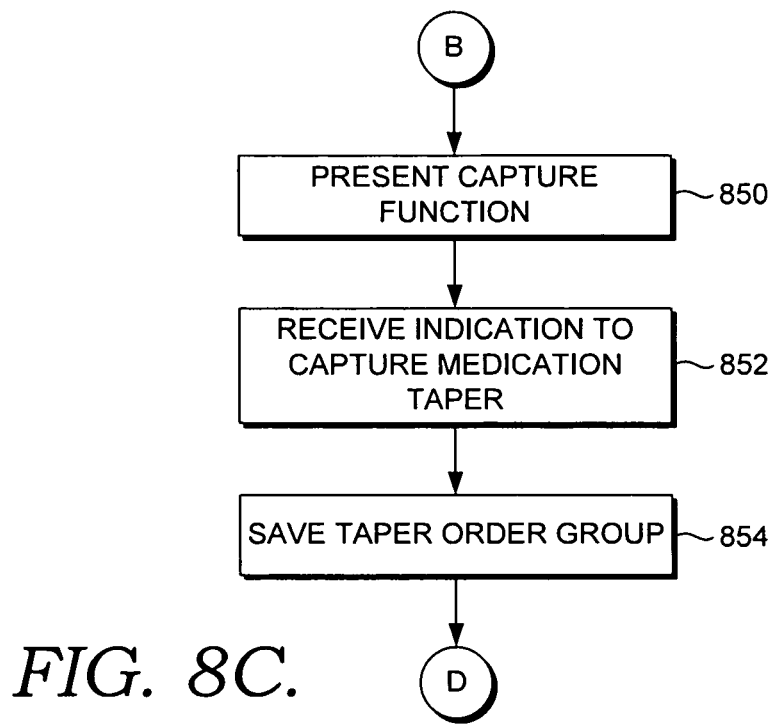
Figure 8D:
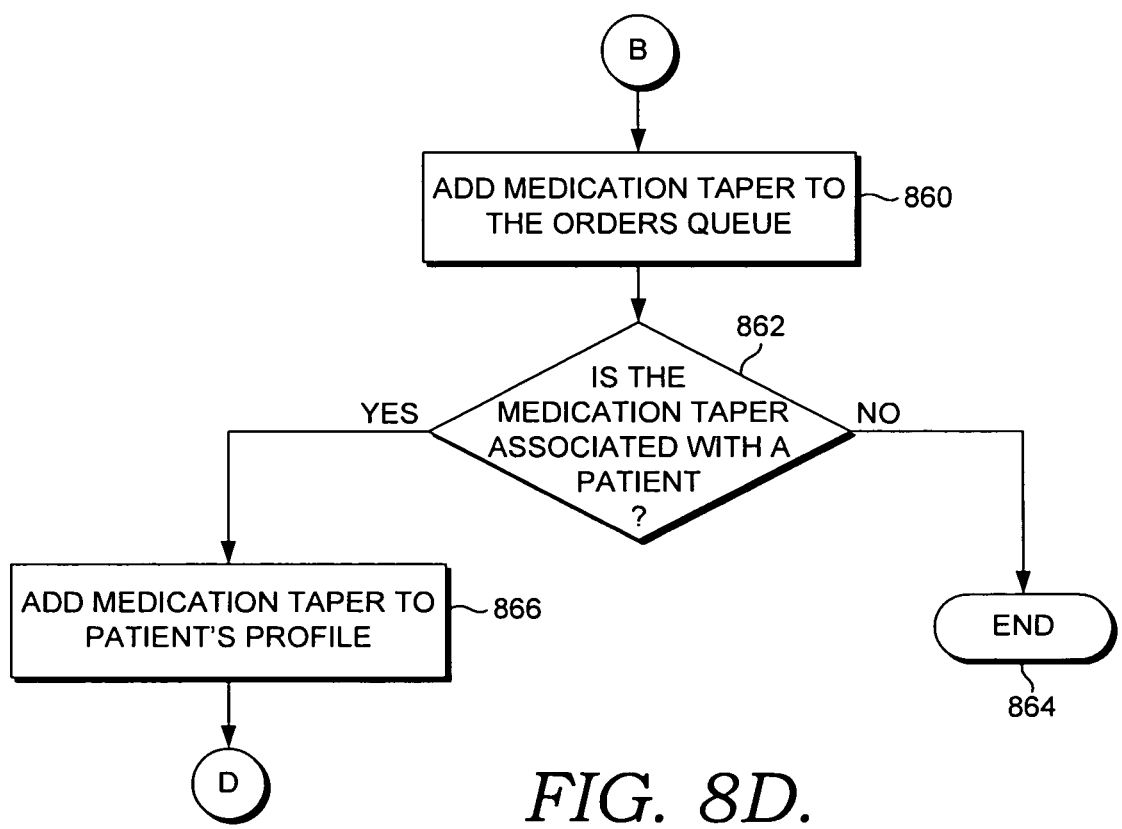

FIGS. 5-7 illustrate exemplary displays of graphical user interfaces for generating a taper worksheet, according to embodiments of the present invention. The taper worksheet may be any electronic display wherein clinicians have access to the worksheet to view and input data. The taper worksheet described herein may be displayed on user device 216 of FIG. 2. A clinician can interact with the medication taper worksheet using well known input components—such as, for example, a mouse, joystick, stylus, touch screen, keyboard, or the like.

By way of illustration only, the exemplary displays of FIGS. 5-7 show views of screens displayed to a clinician in generating a taper worksheet. With reference to FIG. 5, suppose, for instance, that a clinician accesses John Doe's record within a prescription ordering service 500. In accessing John Doe's record within a prescription ordering service 500, the clinician may view, among others items, orders for signature 510, plans 512, suggested plans 514, orders 514, and reconciliation history 516. Suppose further that the clinician searches for and selects the medication order "prednisone" as displayed in view 600 of FIG. 6. Upon searching for and selecting medication order "prednisone" 610, a taper availability notice 612 is presented due to the appropriateness of a medication taper for "prednisone."

The clinician may select to convert the medication order "prednisone" 610 into a medication taper. Upon selection to generate a medication taper, such as clicking on taper availability notice 612 of FIG. 6, the medication taper options are determined and the medication taper worksheet 700 of FIG. 7 is presented. Medication taper worksheet 700 of FIG. 7 includes default data associated with the original medication order "prednisone" 610 of FIG. 6, i.e., a start dose of 45, a start date of Jan. 25, 2007, and a start time of 1708.

Turning now to FIG. 8, a flow diagram showing a method for generating a medication taper, in accordance with an embodiment of the present invention, is illustrated and designated generally as reference numeral 800. Method 800 may be implemented on the above-described exemplary computing system environment (FIG. 1) and, by way of example only, may be utilized by a clinician to prepare and/or submit a medication taper.

Initially, as indicated at block 810, it is determined which medication taper fields are required to receive input. Subsequently, at block 812, it is determined if data has been input into all required medication taper fields. If it is determined that not all fields are completed, the method ends, as indicated at block 814. If, however, it is determined that data has been input into all required medication taper fields, a calculating functionality is enabled at block 816. Subsequently, at block 818, it is determined whether an indication to calculate the planned regimen has been received. If it is determined that an indication to calculate the planned regimen has not been received, the method ends, as indicated at block 820. If it is determined that an indication to calculate the planned regimen has been received, data associated with a medication taper is received at block 822. Subsequently, at block 824, a planned regimen is calculated. The planned regimen and/or order details are then presented. This is indicated at block 826.

At block 828, it is determined if the clinician desires to modify the medication taper, capture the medication taper to favorites, or complete the medication taper. If it is determined that the clinician desires to modify the medication taper, at block 830 it is determined if the clinician desires to add a medication order, delete a medication order, or modify a medication order. If the clinician desires to add a medication order, a new medication order row is added at block 832. At block 834, default data is presented in the new medication order row. Subsequently, at block 836, input pertaining to the new medication order is received. The order details are updated at block 844. The method then returns to the step indicated at block 828, and it is determined what action the clinician desires to perform.

If, however, it is determined, at block 830, that the clinician desires to modify a medication order, an indication of the medication order for which a modification is desired is received at block 838. Subsequently, at block 840, modifications are received. The order details are then updated, as shown at block 844. The method then returns to the step indicated at block 828 and it is determined what action the clinician desires to perform.

Alternatively, if it is determined, at block 830, that the clinician desires to delete a medication order, the medication order is deleted at block 842. The order details are subsequently updated, as shown at block 844. The method then returns to the step indicated at block 828 and it is determined what action the clinician desires to perform.

Returning now to block 828, if it is determined that the clinician desires to capture the medication taper, a capture function is presented to the clinician at block 850. In some embodiments, input may be received pertaining to the name of the captured medication taper and the file location for saving the medication taper. Subsequently, an indication to capture the medication taper is received at block 852. The medication taper is captured at block 854. The method then returns to the step indicated at block 828 and it is determined what action the clinician desires to perform.

Again returning to block 828, if it is determined that the clinician desires to complete the medication taper, the medication taper is added to the orders queue at block 860. At block 862, it is determined if the medication taper is associated with a patient. If it is determined that the medication taper is not associated with a patient, the method ends, as indicated at block 864. If, however, it is determined that the medication taper is associated with a patient, the medication taper is added to the patient's profile. This is indicated at block 866.

FIGS. 9-12 illustrate exemplary displays of graphical user interfaces for generating a medication taper, according to embodiments of the present invention. The medication taper is generated by utilizing a taper worksheet. The taper worksheet may be any electronic display wherein clinicians have access to the worksheet to view and input data. The taper worksheet described herein may be displayed on user device 216 of FIG. 2. A clinician can interact with the taper worksheet using well known input components—such as, for example, a mouse, joystick, stylus, touch screen, keyboard, or the like.

Figure 9:
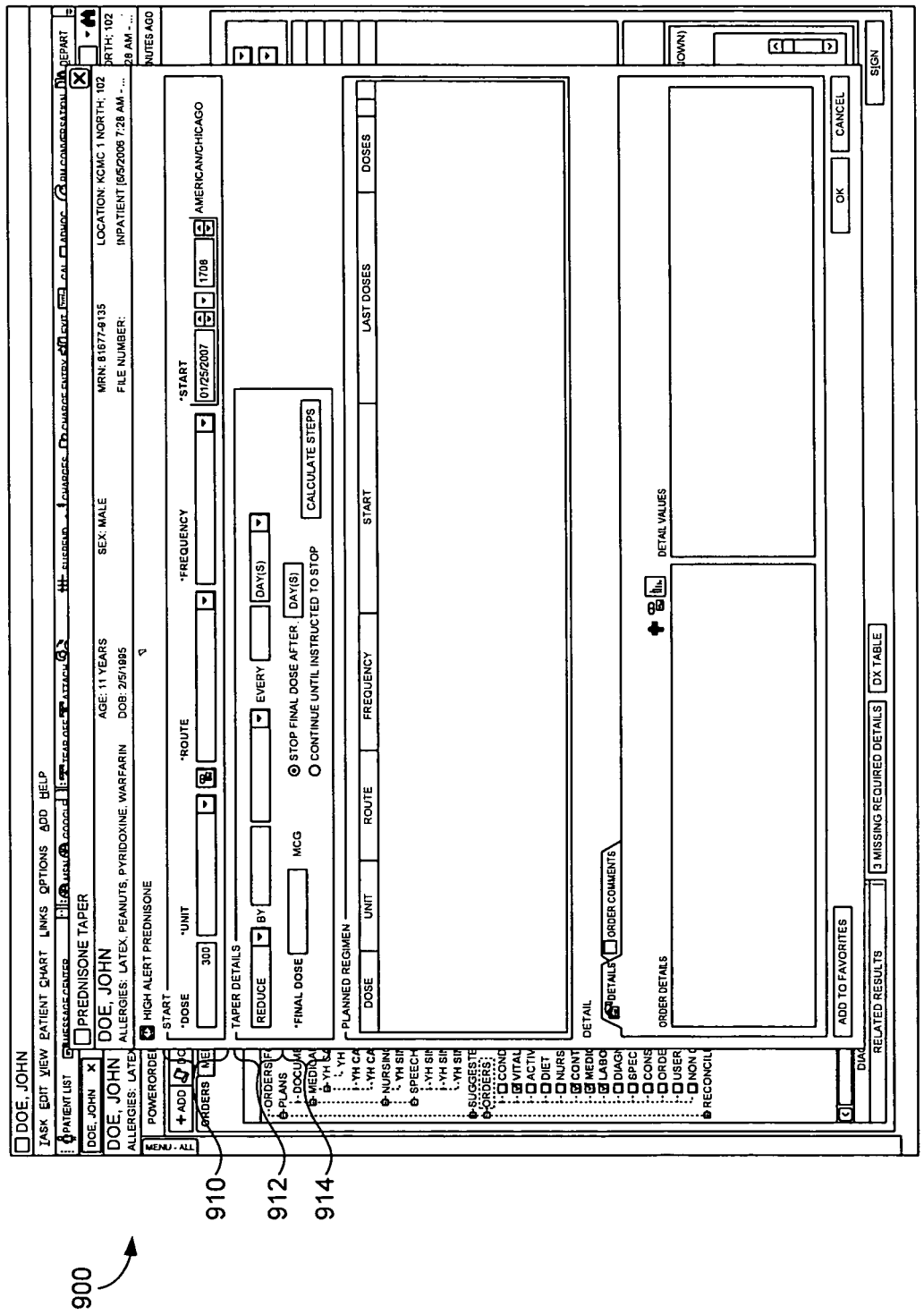
FIG. 9 is an illustrative screen display of an exemplary user interface for viewing a medication taper worksheet, in accordance with an embodiment of the present invention.
Figure 10:
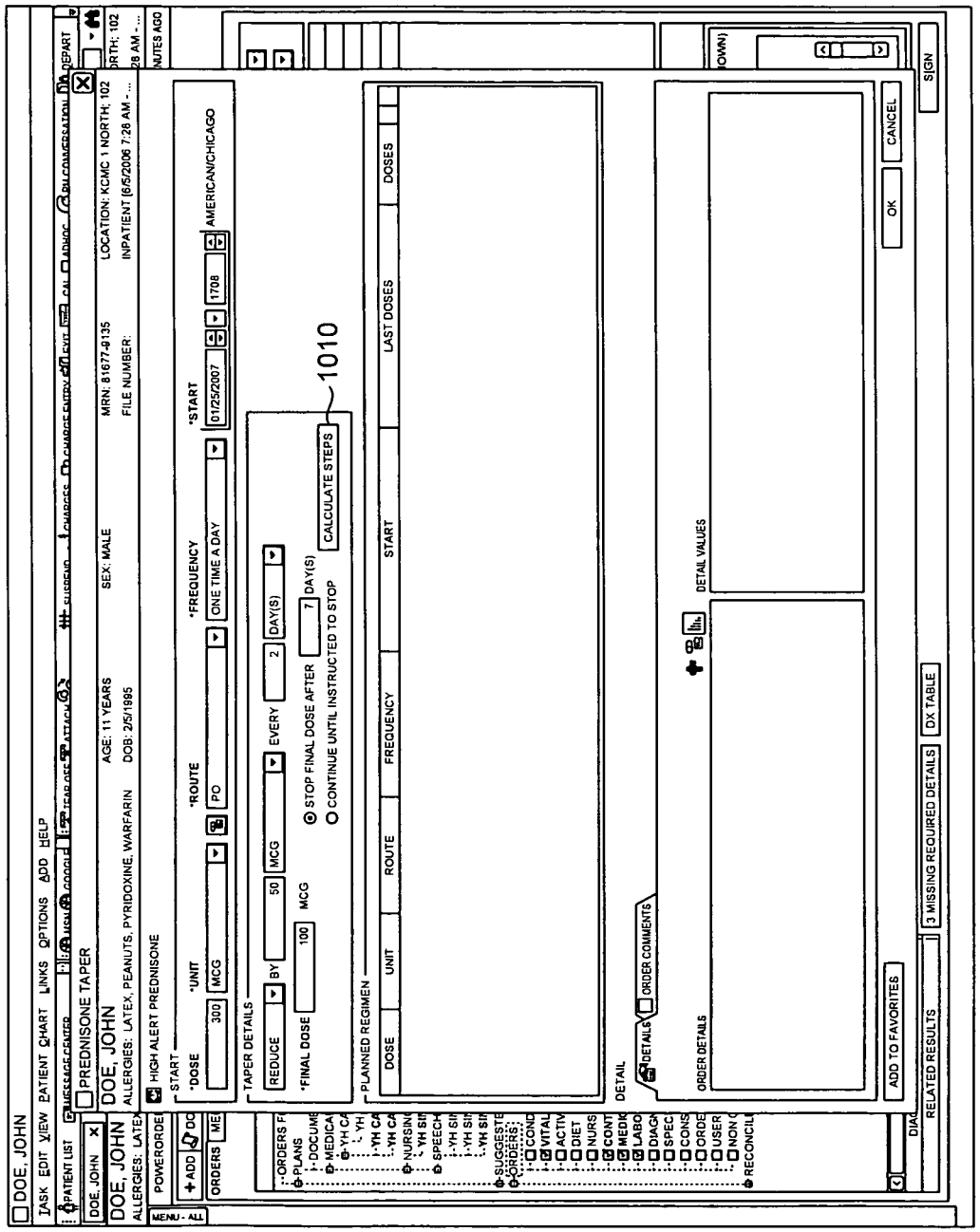
FIG. 10 is an illustrative screen display of an exemplary user interface for viewing a medication taper worksheet having input in a plurality of medication taper fields, in accordance with an embodiment of the present invention.
Figure 11:
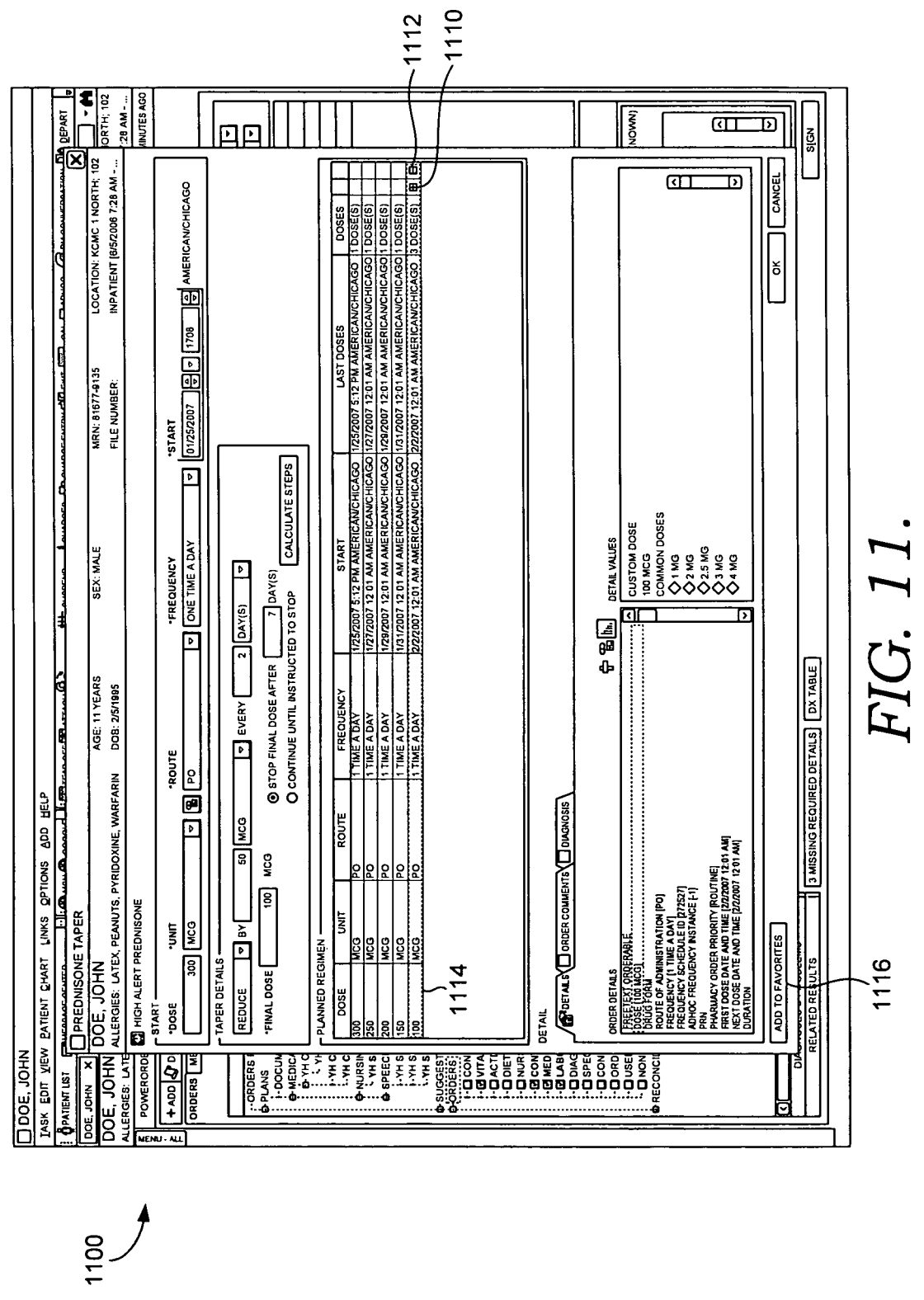
Figure 12:
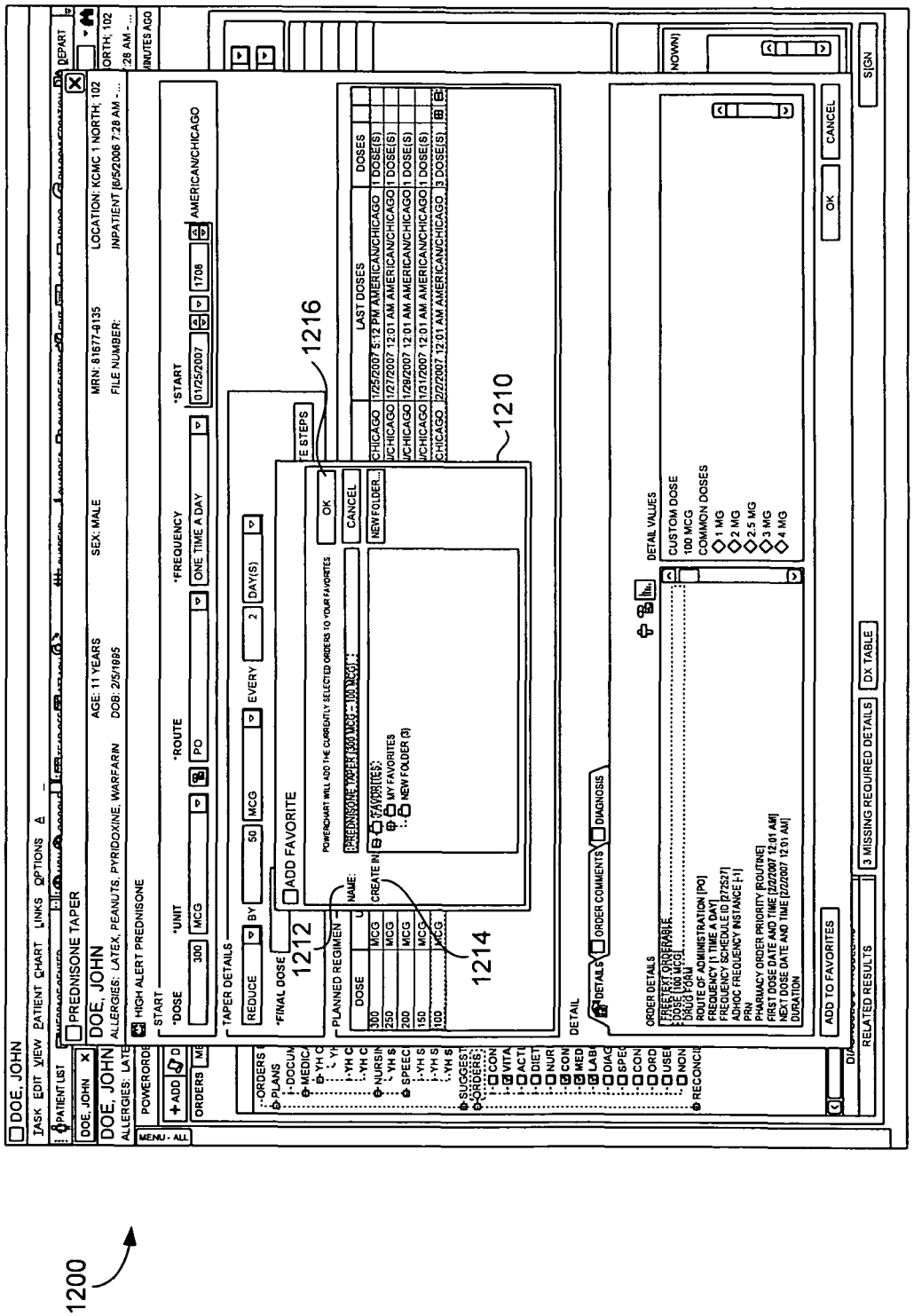
FIG. 12 is an illustrative screen display, in accordance with an embodiment of the present invention, of an exemplary user interface for viewing a favorites dialogue box.

By way of illustration only, the exemplary displays of FIGS. 9-12 show views of screens displayed to a clinician in generating a medication taper. With reference to FIG. 9, suppose, for instance, that a clinician accesses a medication taper worksheet 900. In some embodiments, the medication taper worksheet 900 may include default data in one or more medication taper fields. Upon accessing taper worksheet 900, the clinician inputs data into the start dose area 910, the taper details area 912, and the final dose area 914 of FIG. 9. As displayed in view 1000 of FIG. 10, data has been input into all of the required medication taper fields. Accordingly, the calculating functionality is enabled, e.g., "calculate steps" button 1010. Clinician may select to calculate the planned regimen by, for example, selecting the "calculate steps" button 1010 of FIG. 10. Upon selecting to calculate the planned regimen, the planned regimen is presented to the clinician, as displayed in view 1100 of FIG. 11.

At this point, the clinician has the option of modifying one or more medication orders of the planned regimen, adding the medication order to favorites, or completing the medication taper. Suppose the clinician desires to modify the medication taper. The clinician may select the medication order adding button 1110 to add a medication after the last medication order 1114, select the medication order deletion button 1112 to delete the last medication order 1114, or modify the last medication order 1114 by selecting the last medication order 1114 displayed in the planned regimen and modifying the last medication order 1114.

Figure 13:
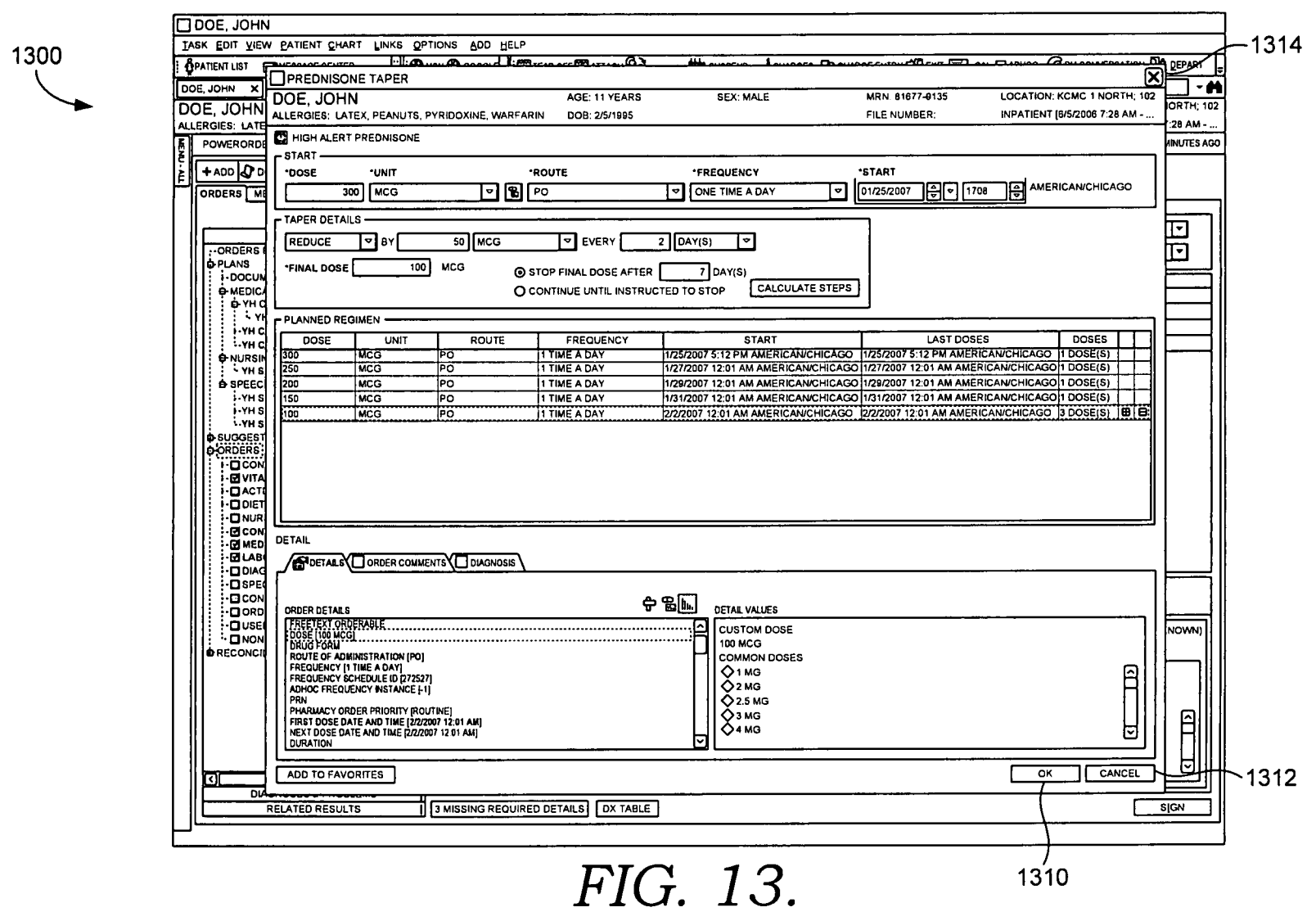

Suppose further that the clinician desires to add the medication order to a favorites folder. In such a case, the clinician may select to capture the medication taper, such as by clicking on the "add to favorites" button 1116. Upon selecting to add to favorites, a dialogue box 1210 is presented as displayed in view 1200 of FIG. 12. The dialogue box 1210 allows the clinician to name the file 1212 and select the folder 1214 for capturing the medication taper. In one embodiment, the file name 1212 and folder 1214 may be a default. The clinician may then add the medication taper to favorites by selecting the "OK" button 1216. Upon selecting the "OK" button 1216, the clinician is returned to the view of the completed medication taper worksheet as displayed in view 1300 of FIG. 13.

Now suppose that the clinician desires to complete the medication taper. The clinician may select to submit the medication taper, such as by clicking on the "OK" button 1310. Alternatively, if the clinician decided that the medication order is unsatisfactory, the clinician may select to cancel the medication taper, such as by clicking on the "Cancel" button 1312 or the "close" button 1314.

Figure 14A:
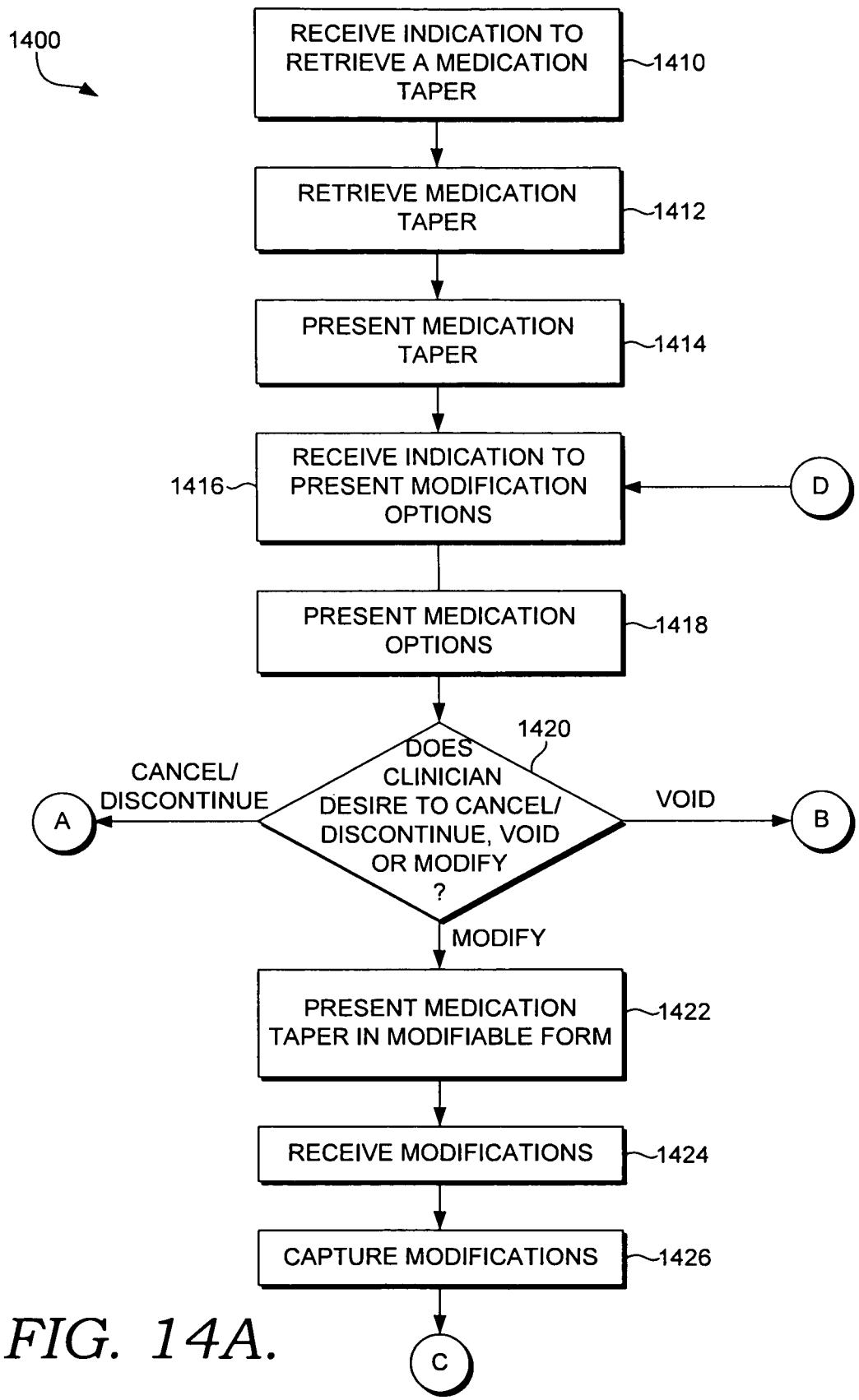
FIGS. 14A and 14B are a flow diagram showing a method for managing a medication taper, in accordance with an embodiment of the present invention.
Figure 14B:
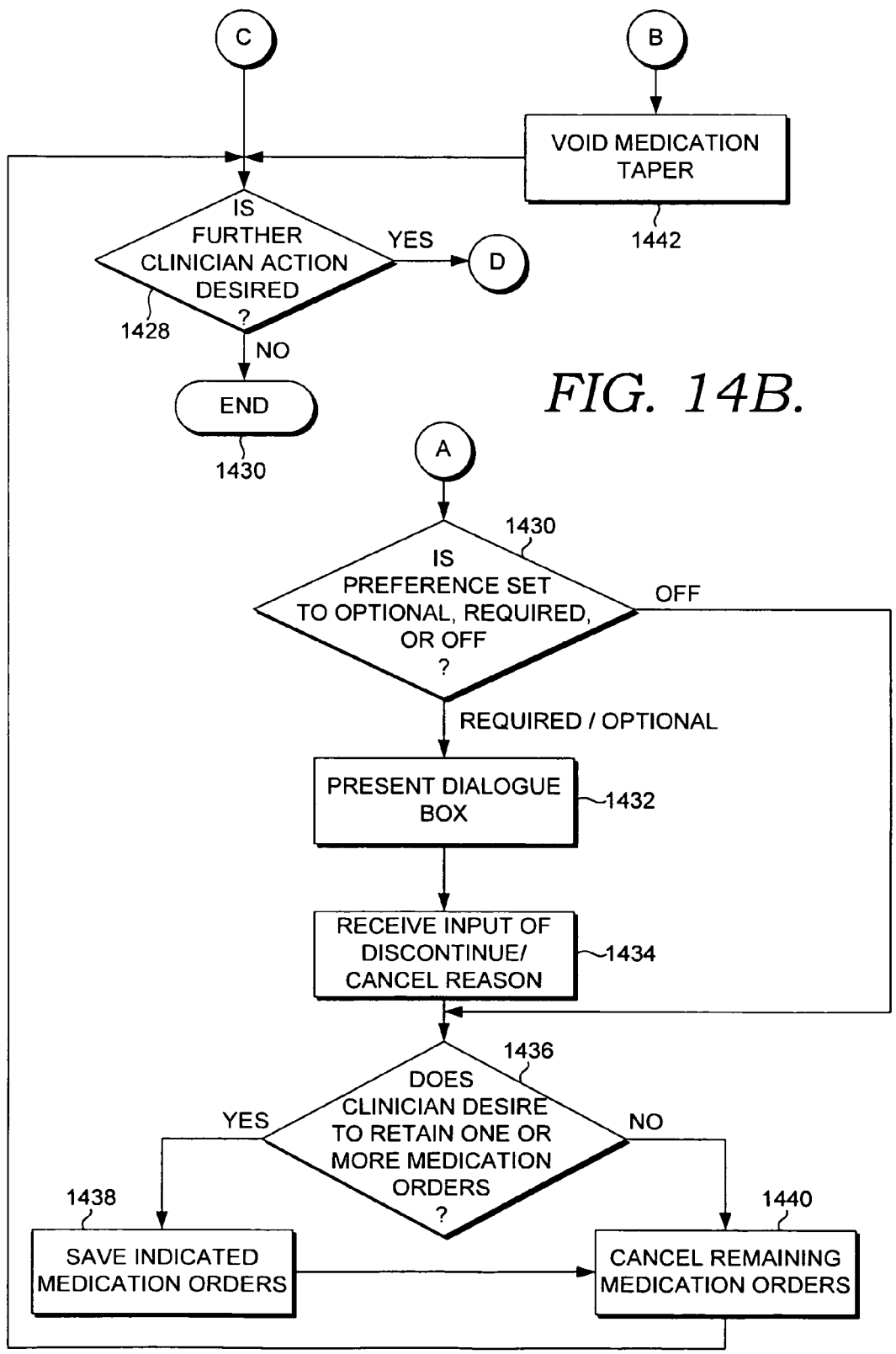

Turning now to FIG. 14, a flow diagram showing a method for managing a medication taper, in accordance with an embodiment of the present invention, is illustrated and designated generally as reference numeral 1400. Method 1400 may be implemented on the above-described exemplary computing system environment (FIG. 1) and, by way of example only, may be utilized by a clinician to modify a medication taper.

Initially, as indicated at block 1410, an indication to retrieve a medication taper is received. At block 1412, the medication taper order is retrieved. The medication taper is presented at block 1414. Subsequently, at block 1416, an indication to present modification options is received at block 1416, e.g., a clinician right clicks on a medication order. The modification options are presented at block 1418. In one embodiment, if the indication to present modification options is directed to a medication order, only modification options pertaining to medication orders are presented. If the indication to present modification options is directed to a medication taper, only modification options pertaining to medication taper are presented. It is then determined if the clinician desires to cancel/discontinue a medication taper, void a medication taper, or modify a medication taper. This is indicated at block 1420.

If it is determined that the clinician desires to modify a medication taper, the medication taper is presented in modifiable form at block 1422. Subsequently, as indicated at block 1424, modifications are received. At block 1426, the modifications are captured. It is then determined if the clinician desires further action. This is indicated at block 1428. If it is determined that no further clinician action is desired, the method ends, as indicated at block 1430. If, however, it is determined that further clinician action is desired, the method then returns to the step indicated at block 1416 and an indication to present modification options is received.

Referring again to block 1420, if it is determined that the clinician desires to cancel or discontinue a taper order, it is determined at block 1430 if the cancel preference is set to optional, required, or off. If the preference is set to optional or required, a dialogue box is presented at block 1432. Subsequently, at block 1434, input of discontinue or cancellation reason is received. It is then determined if the clinician desires to retain one or more medication orders, as indicated at block 1436. If it is determined that the clinician desires to retain one or more orders, the indicated orders are saved at block 1438 and the remaining medication orders are canceled at block 1440. If, however, it is determined that the clinician does not desire to retain one or more orders, the all the medication orders are canceled at block 1440 such that the entire medication taper is canceled. After orders are canceled at block 1440, it is determined if the clinician desires further action, as indicated at block 1428. If it is determined that no further clinician action is desired, the method ends, as indicated at block 1430. If, however, it is determined that further clinician action is desired, the method then returns to the step indicated at block 1416 and an indication to present modification options is received.

Returning now to block 1430, if the cancel preference is set to off, it is determined whether the clinician desires to retain one or more medication orders. This is indicated at block 1436. If it is determined that the clinician desires to retain one or more medication orders, the specified medication orders are saved at block 1438 and the remaining medication orders are canceled at block 1440. If, however, the clinician does not desire to retain one or more medication orders, all the medication orders are canceled at block 1440. After medication orders are canceled at block 1440, it is determined if the clinician desires further action, as indicated at block 1428. If it is determined that no further clinician action is desired, the method ends, as indicated at block 1430. If, however, it is determined that further clinician action is desired, the method then returns to the step indicated at block 1416 and an indication to present modification options is received.

Again returning to block 1420, if it is determined that the clinician desires to void a medication taper, the medication taper is voided at block 1442. Subsequently, it is determined if the clinician desires further action. This is indicated at block 1428. If it is determined that no further clinician action is desired, the method ends, as indicated at block 1430. If, however, it is determined that further clinician action is desired, the method then returns to the step indicated at block 1416 and an indication to present modification options is received.

FIGS. 15-19 illustrate exemplary displays of graphical user interfaces for managing a medication taper, according to embodiments of the present invention. The medication taper is managed by accessing and utilizing a management information computing system. The prescription ordering service may include any electronic display wherein clinicians have access to view medication tapers and modify medication tapers. The prescription ordering service described herein may be displayed on user device 216. A clinician can interact with the prescription ordering service using well known input components—such as, for example, a mouse, joystick, stylus, touch screen, keyboard, or the like.

Figure 15:
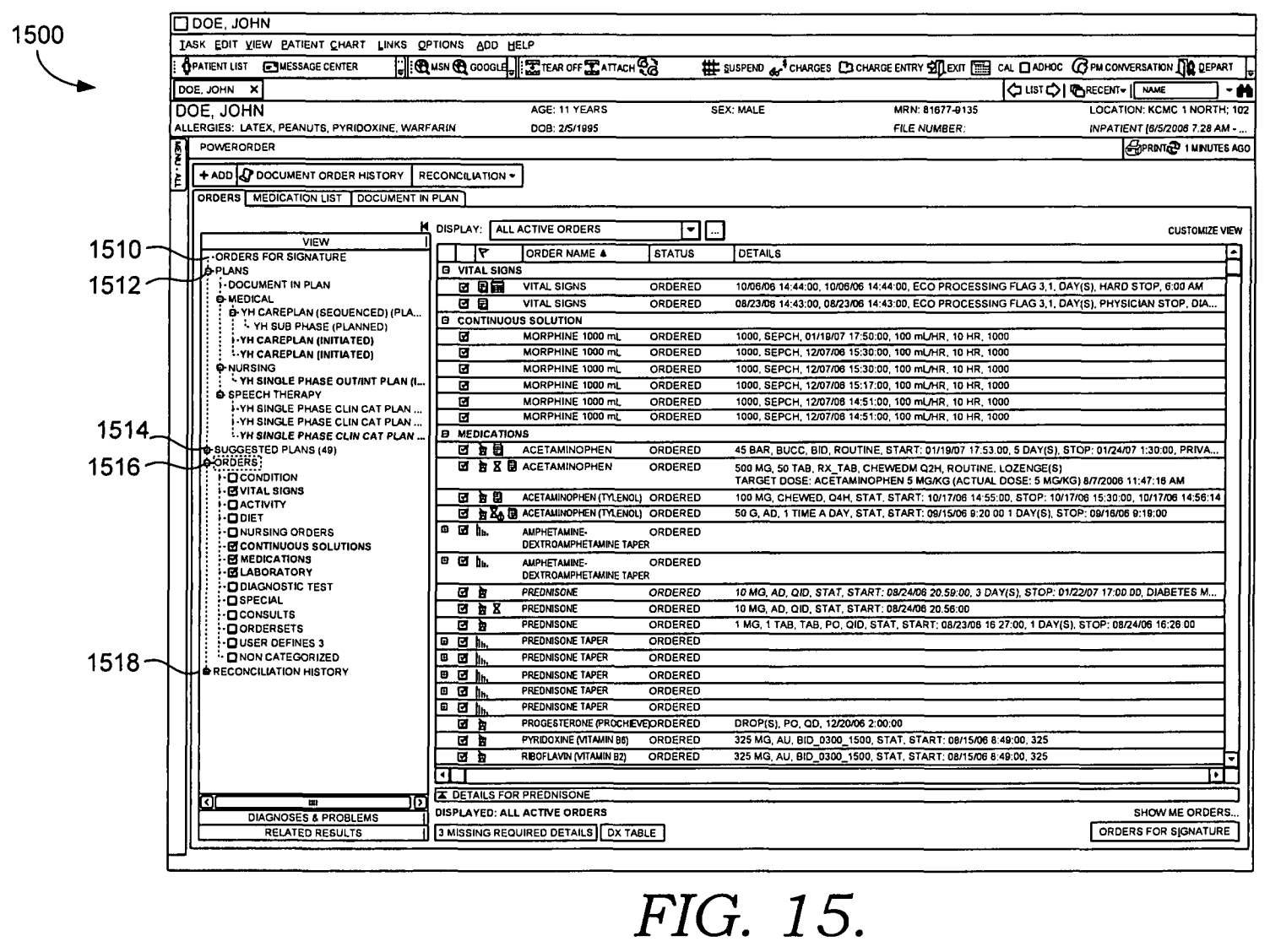
Figure 16:
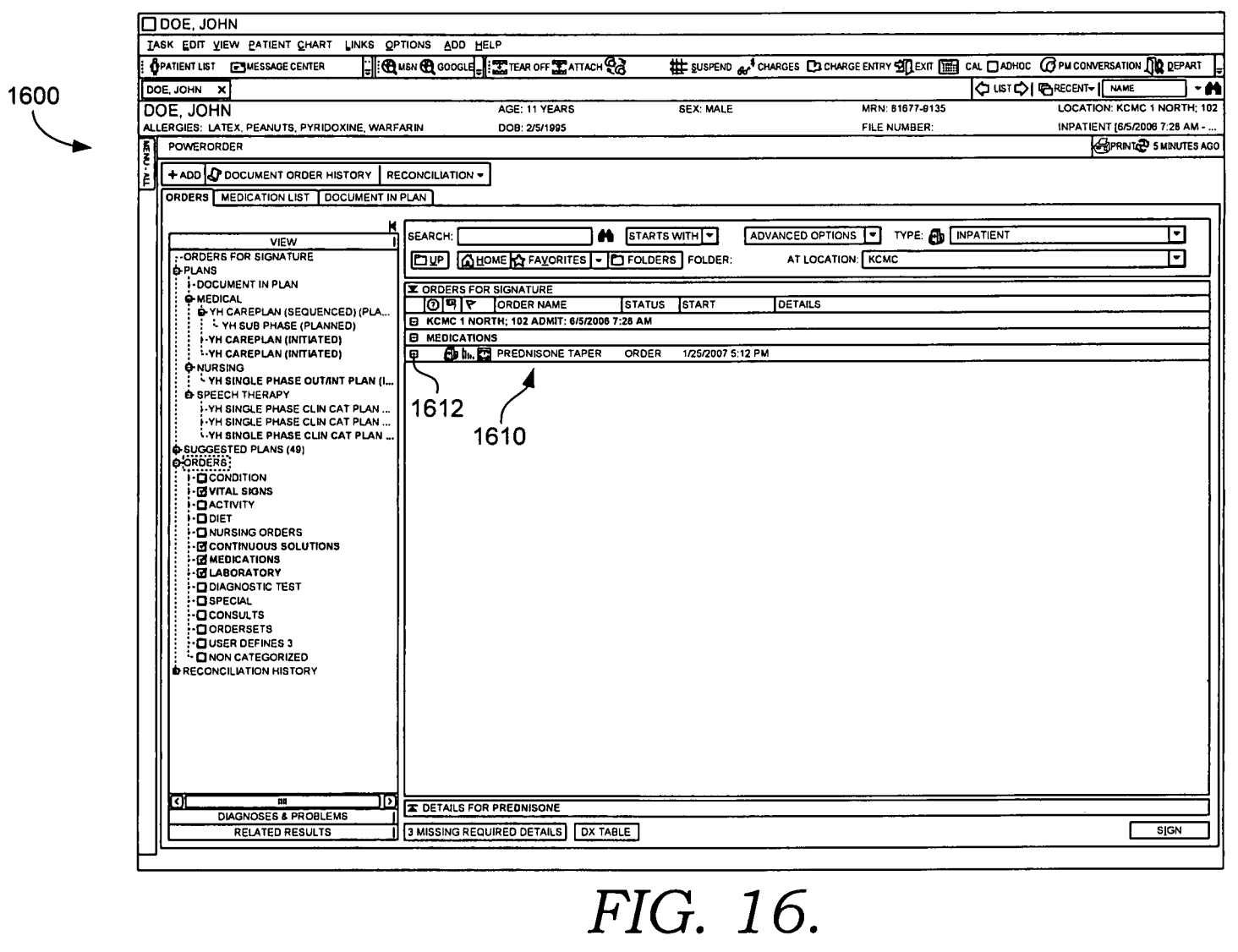
Figure 17:
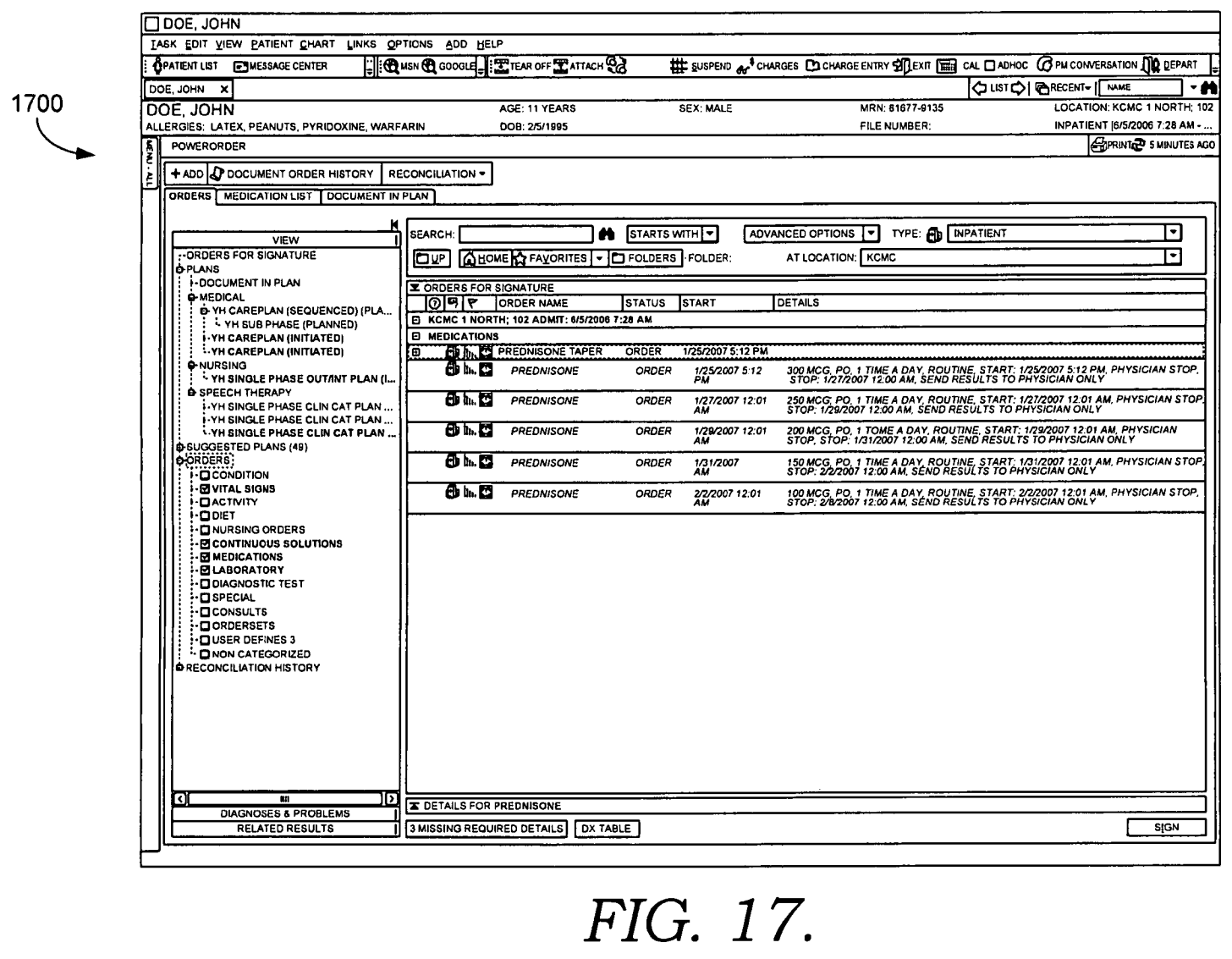
Figure 18:
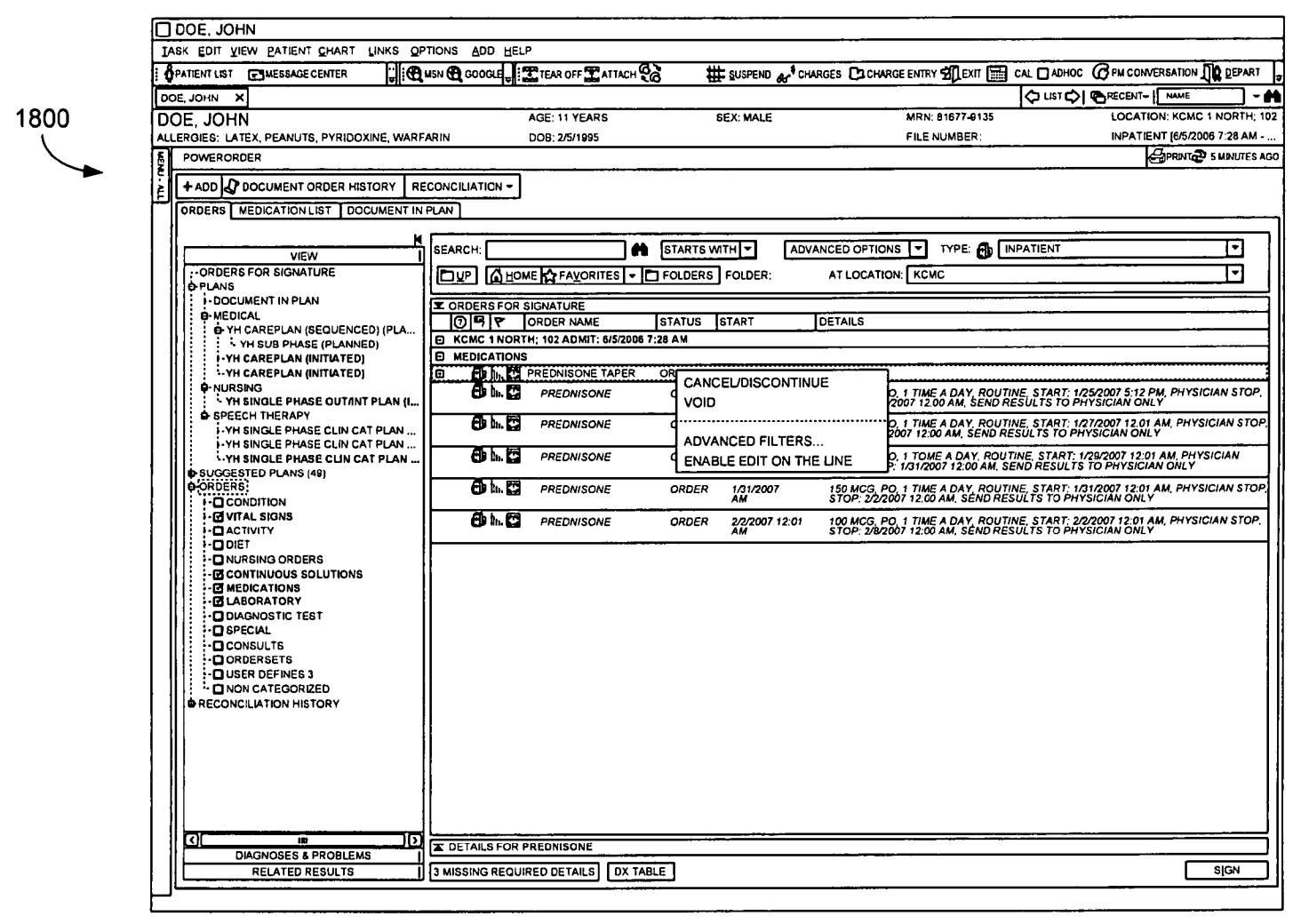
Figure 19:
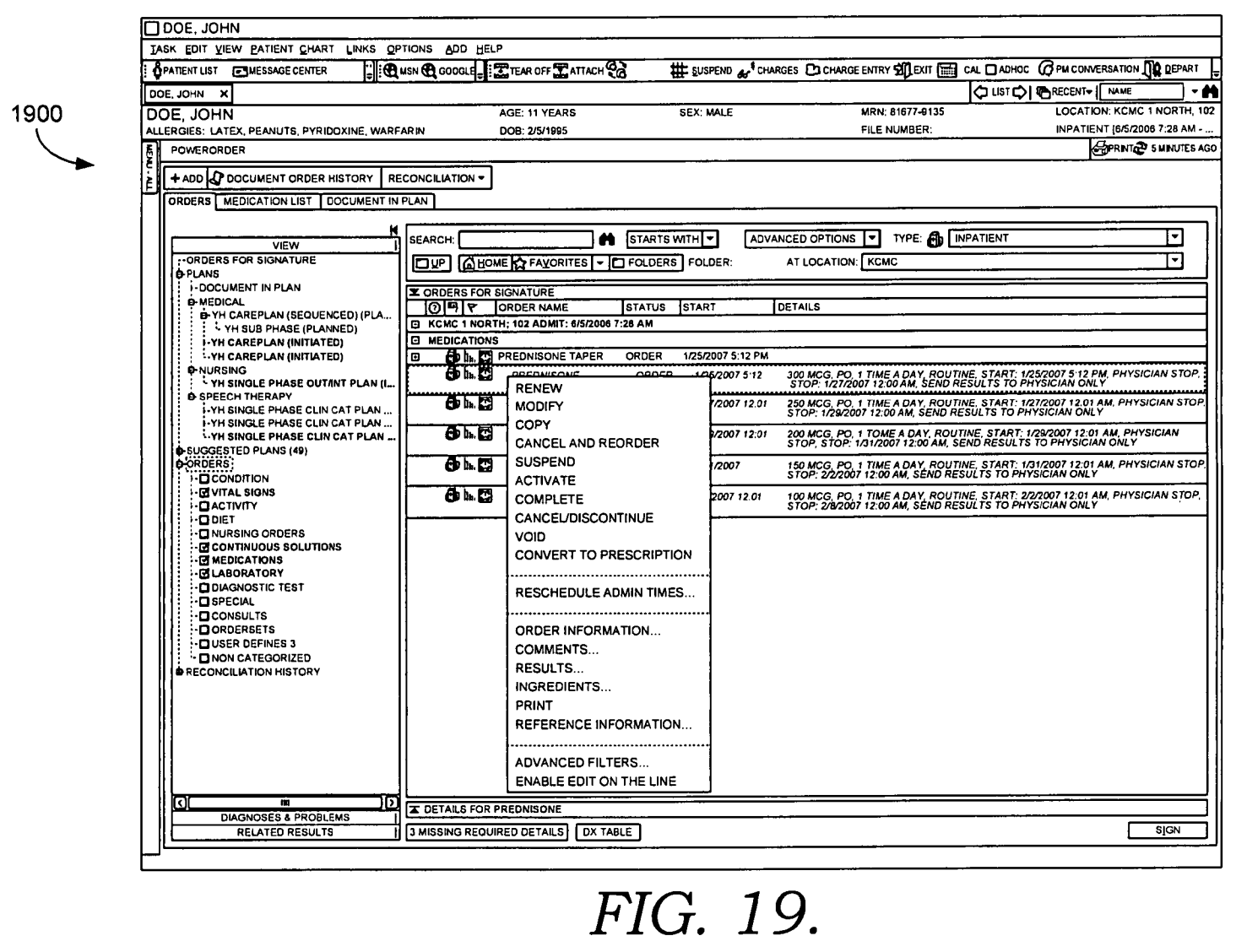

By way of illustration only, the exemplary displays of FIGS. 15-19 show views of screens displayed to a clinician in managing a medication taper. With reference to FIG. 15, suppose, for instance, that a clinician accesses John Doe's record within a prescription ordering service 1500. In accessing John Doe's record within a prescription ordering service 1500, the clinician may view, among others items, orders for signature 1510, plans 1512, suggested plans 1514, orders 1516, and reconciliation history 1518. Suppose further that the clinician searches for and selects the medication taper "prednisone" as displayed in view 1600 of FIG. 16. Upon searching for and selecting medication taper "prednisone" 1610, the clinician desires to view the specific medication orders of the medication taper "prednisone" 1610. Accordingly, the clinician selects to view the specific medication orders, such as be selecting the "expand" button 1612. Upon selecting to view the expanded view of the medication taper, the clinician is presented with the expanded view 1700 of FIG. 17.

Suppose the clinician desires to cancel the medication taper. In such an instance, the clinician indicates a desire to view the options for modifying the medication taper, e.g., right click on the medication taper to view FIG. 1800 of FIG. 18. The clinician is presented with, among other options, the option to cancel/discontinue or void. In another instance, the clinician may desire to modify a medication order. Accordingly, the clinician indicates a desire to view the options for modifying a medication order, e.g., right click on a medication order to view FIG. 1900 of FIG. 19. The clinician is presented with the options to renew, modify, copy, cancel and reorder, suspend, activate, complete, cancel/discontinue, void, convert to prescription, and the like. In one embodiment, any modification options pursued by the clinician may be automatically captured upon the modification.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. A user interface embodied on at least one computer storage medium, the user interface for generating medication tapers, the user interface comprising:
   a taper availability notice area configured to provide a notification that a medication taper is clinically appropriate for a medication based on a type of the medication being determined to be clinically appropriate for association with two or more medication orders having increasing or decreasing medication doses or frequencies of administration, the taper availability notice being displayed via a computing device;
   a start dose display area configured to receive one or more data elements pertaining to a first dose of the medication;
   a taper details display area configured to receive one or more data elements pertaining to a change relative to the first dose of the medication;
   a final dose display area configured to receive one or more data elements pertaining to a final dose of the medication; and
   a selectable calculation indicator display area configured to display a calculation indicator, selection of which initiates calculation of a planned regimen.

2. The user interface of claim 1, further comprising a planned regimen display area configured to display the planned regimen, wherein the planned regimen includes a set of orders defining a medication taper for the medication.

3. The user interface of claim 1, further comprising an order details display area configured to display one or more order details and detail values pertaining to the planned regimen.

4. The user interface of claim 1, wherein the one or more data elements pertaining to the first dose of the medication includes one or more of a dose field configured for receiving a starting dose value, a unit field configured for receiving a starting dose unit, a route field configured for receiving a medication administration route, a frequency field configured for receiving a medication frequency of administration, a start date field configured for receiving a start date for administration of the medication; and a start time field configured for receiving a start time for administration of the medication.

5. The user interface of claim 1, wherein the one or more data elements pertaining to a change relative to the first dose of the medication includes one or more of an increment/decrement field configured for receiving an indication whether the change relative to the first dose is incremented or decremented; a taper dose field configured for receiving a value by which the medication dose is to be changed relative to the first dose, a taper dose unit field configured for receiving a unit by which the medication dose is to be changed relative to the first dose, a dose duration field configured for receiving a duration value after which the change relative to the first dose is to occur; and a dose duration unit field configured for receiving a unit to be associated with the duration value.

6. The user interface of claim 1, wherein the one or more data elements pertaining to a final dose of the medication includes one or more of a final dose field configured for receiving a final dose value, a final dose unit field configured for receiving a final dose unit, a stop field configured for receiving an indication whether a final dose of the medication is to be stopped after a specified period of time; a stop duration field configured for receiving a unit value after which the final dose is to be stopped; and a continuation field configured for receiving an indication that the final dose is to continue until further instruction is received.

7. The user interface of claim 1, wherein each of the start dose display area, the taper details display area, and the final dose display area are configured to receive only clinically appropriate taper details for the medication.

8. The user interface of claim 1, further comprising one or more of a selectable medication order adding indicator configured for permitting addition of an additional medication order to the one or more medication orders included in the planned regimen upon selection thereof and a selectable medication order deletion indicator configured to permit deletion of at least one of the one or more medication orders included in the planned regimen upon selection thereof.

9. The user interface of claim 1, further comprising a selectable add to favorites indicator configured to permit capturing of the medication taper to a favorites storage location upon selection thereof.

10. A user interface embodied on at least one computer storage medium, the user interface for managing medication tapers, the user interface comprising:
   an orders display area displaying one or more orders associated with a patient's electronic medical record, at least one of the one or more orders having an indicator associated therewith indicating the at least one order comprises a set of orders defining a medication taper, the orders display area being displayed via a computing device,
   wherein the at least one order includes a selectable indicator associated therewith, selection of which initiates display of one or more additional details associated with the medication taper, and
   wherein each order of the set of orders defining the medication taper includes a selectable indicator associated therewith, selection of which permits a modification to be made to the corresponding order within the medication taper without modifying the other orders within the medication taper.

11. The user interface of claim 10, wherein the one or more additional details associated with the medication taper comprises a selectable expansion indicator, selection of which initiates display of the set of orders defining the medication taper.

12. The user interface of claim 10 further comprising an alert display area configured to display an alert indicating the modification is clinically inappropriate.

13. The user interface of claim 10, wherein the modification to be made to the corresponding order within the medication taper comprises an adjustment of a dosage amount associated with the corresponding order.

14. A user interface embodied on at least one computer storage medium, the user interface for generating medication tapers, the user interface comprising:
   a taper availability notice area configured to provide a notification that a medication taper is clinically appropriate for a medication based on a determination that the medication is deemed clinically appropriate for association with two or more medication orders having increasing or decreasing medication doses or frequencies of administration, the taper availability notice being displayed via a computing device, wherein
      the notification is presented for a first medication when the medication taper is determined to be clinically appropriate for the first medication, and
      the notification is not presented for a second medication when the medication taper is determined to be clinically inappropriate for the second medication; and
   an orders display area configured to display a plurality of orders associated with the medication having increasing or decreasing medication doses or frequencies of administration associated with a patient's electronic medical record, wherein
      in accordance with a selection to modify one of the plurality of orders, presenting only modification options pertaining to modification of a single order independent of a modification of the other orders associated with the medication, wherein selection of a first modification option modifies the single order in accordance with the selection, and
      in accordance with a selection to modify the plurality of orders as a group, presenting only modification options pertaining to modification of the plurality of orders, wherein selection of a second modification option modifies each of the plurality of orders in accordance with the selection.

15. The user interface of claim 14 further comprising an inappropriate change area configured to present an indication that a modification to an order or a plurality of orders is clinically inappropriate when a change is determined to be clinically inappropriate for a specific type of medication associated with the medication taper.

* * * * *